(12) United States Patent
Goohs et al.

(10) Patent No.: US 8,351,035 B2
(45) Date of Patent: Jan. 8, 2013

(54) PARTICULATE DETECTION AND CALIBRATION OF SENSORS

(75) Inventors: Kevin J. Goohs, Greenfield, NH (US); Pedro Lilienfeld, Lexington, MA (US); Dieter Kita, Blackstone, MA (US); John G. Hiss, Franklin, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 453 days.

(21) Appl. No.: 12/777,127

(22) Filed: May 10, 2010

(65) Prior Publication Data

US 2010/0315638 A1    Dec. 16, 2010

Related U.S. Application Data

(60) Provisional application No. 61/177,563, filed on May 12, 2009.

(51) Int. Cl.
*G01N 21/00* (2006.01)
(52) U.S. Cl. ...................................... 356/337; 356/342
(58) Field of Classification Search .................. 356/337, 356/342
See application file for complete search history.

(56) References Cited

U.S. PATENT DOCUMENTS

| | | | |
|---|---|---|---|
| 3,953,127 A | 4/1976 | Ahlquist | |
| 5,349,844 A | 9/1994 | Lilienfeld | |
| 5,886,345 A | 3/1999 | Koster et al. | |
| 6,537,821 B1 | 3/2003 | Rosenblatt et al. | |
| 6,653,150 B1 | 11/2003 | Reed | |
| 6,707,556 B2 | 3/2004 | Turner et al. | |
| 7,111,496 B1 * | 9/2006 | Lilienfeld et al. | ........... 73/28.01 |
| 7,354,553 B2 | 4/2008 | Appel et al. | |

OTHER PUBLICATIONS

International Search Report, Jun. 30, 2010, pp. 2.

* cited by examiner

*Primary Examiner* — Roy M Punnoose
(74) *Attorney, Agent, or Firm* — Chapin IP Law, LLC

(57) ABSTRACT

According to example configurations herein, a fluid sample flow including particulate matter passes through a conduit. One or more optical sensors monitor optical energy scattering off of the particulate matter in the fluid sample flow as it passes through the conduit. A magnitude of the optical energy sensed by the one or more optical sensors varies depending on particulate matter present in the fluid sample flow. An analyzer monitors the magnitude of the optical energy sensed by the one or more optical sensors and detects changes in the optical energy. A change in the optical energy can indicate a change in the particulate matter present in the fluid sample flow. In response to detecting the change in the optical energy, the analyzer initiates one or more functions such as recalibration, purging, execution of diagnostics, etc.

30 Claims, 18 Drawing Sheets

PARTICULATE DETECTION AND CALIBRATION OF SENSORS

RELATED APPLICATION

This application is related to and claims the benefit of earlier filed U.S. Provisional Patent Application Ser. No. 61/177,563 entitled "Particulate Detection and Calibration of Sensors," filed on May 12, 2009, the entire teachings of which are incorporated herein by this reference.

BACKGROUND

Ambient air quality can affect people's health. The lower the air quality, the greater the risk for health-related problems induced by the ambient air.

One parameter of air quality is the amount of particulate matter present in an air sample, which can originate from anthropogenic emissions (e.g., power generation, metal refineries, cement production, and waste incineration) or atmospheric formation from gaseous precursors. Conventional particulate matter sampling devices can be used to measure a mass concentration of particulate matter within ambient air, source emissions, gases, or other fluids to determine ambient air quality. A conventional particulate matter sampling device typically can provide a warning to a user when the device detects a condition of relatively low air quality (e.g., a relatively large particulate mass concentration within the air) or a decrease in the ambient air quality based upon an increase in particulate mass concentration measured over a particular time period.

Continuous particulate monitoring in stack effluent streams is becoming a growing concern in the US as well as abroad. Accordingly, stricter standards have been or will be implemented to cut back on such pollution. As a result of tightening standards, new methods are being sought to accurately measure the primary particulate emissions from industrial sources using a direct monitoring device.

Several sensing techniques provide continuous direct monitoring of particulate mass concentration. For example, the sensing techniques used for particulate monitoring include mass sensing methods such as an inertial mass measurement instrument (i.e., tapered element oscillating microbalance or TEOM), beta radiation attenuation and optical sensing methods such as light scattering photometry or nephelometry.

In a conventional inertial mass measurement instrument, an oscillating element in a microbalance is provided with a filter on its oscillating end for the entrapment of matter whose mass is to be determined by passing the medium containing such matter therethrough. The oscillating element itself is hollow and the medium passes first through the filter and then through the oscillating element. The measurement of mass can be calculated based on a change in the oscillation frequency. As the collection of aerosol accumulates on the filter, the mass increases, thereby decreasing the frequency of oscillation. By measuring only the change in frequency, one can determine the gain in the aerosol mass on the collection medium.

Beta radiation attenuation devices typically include a mass sensing stage and a particle collection stage. The mass sensing stage includes a beta particle radiation source, typically carbon-14 or krypton-85, and a beta particle detector, typically a Geiger-Muller detector, plastic scintillator, proportional counter or an ionization chamber. The particle collection stage typically includes a filter and vacuum source. The mass sensing stage will position the filter between the beta particle radiation source and the beta particle detector. Some devices are known to combine the stages for simultaneous mass collection and mass sensing. Beta radiation attenuation devices exhibit a substantially exponential attenuation characteristic as a function of the mass per unit area collected by the filter between the radiation source and the radiation detector. For example, during operation, ambient air (or another gas) flows through the filter and the filter collects particulate matter present within the ambient air over time. As the amount of particulate matter collected by the filter increases, the particulate matter attenuates the beta particles emitted from the radiation source (i.e., the beta particle detector senses less radiation from the beta source) as detected by the detector. Because the attenuation of the beta radiation detected by beta particle detector is related to the mass of the particulate matter collected by the filter and does not substantially depend upon the type or compound of material collected by the filter, a beta radiation signal produced by the beta radiation attenuation device indicates a particulate mass concentration of particulate mater within an air sample.

Conventional beta radiation attenuation devices, and other mass sensing devices that utilize a filter to collect particulate matter within an air sample, sometimes utilize temperature and humidity conditioning elements to remove liquid water from the air sample. Should the filter collect liquid water over time, the liquid water will be measured as mass and can affect the accuracy of the device's detection of particulate mass within the air sample.

In conventional particulate monitoring devices, prior to the air sample reaching the filter, the device will either reduce the sample relative humidity by applying heat, use a permeation drying technique to remove water content from the sample stream, or dilute the sample with clean dry air of a considerably lower dewpoint. By reducing the humidity or percentage of water content within the air sample the particulate matter detection accuracy is improved.

Another type of conventional particulate mass sensing device is a light scattering photosensitive device called a nephelometer. Light scattering photometry devices, such as nephelometry devices, measure the irradiance of light scattered by particles passing through a sensing volume. Typical light scattering photometry devices include an incident light beam and detection optics or sensors that measure the strength of the light beam and the intensity of the light scattered by the particles and carrier gas. During operation, ambient air or another gas flows through a sensing volume defined by an intersection of the illuminating beam and the field of view of the sensing optics. As the air flows through the sensing volume, the light scattering photometer illuminates particles present within the sensing volume and the optics and associated photosensitive measuring circuitry detect the light scattered by the particles. For an ambient air sample having a fixed size distribution of particles with invariant density and index of refraction, the intensity of light scattered by the particles within the air sample is directly proportional to the mass concentration of the particles within the air sample. Light scattering photometry or nephelometry devices, therefore, allow real-time (i.e., substantially instant) measurement of particulate mass concentration of ambient air.

BRIEF DESCRIPTION

Conventional methods for determining a concentration of particulate matter in a gas sample suffer from a number of deficiencies. For example, conventional methods of measuring particulate concentrations do not have the ability to accurately detect low-level concentrations of particulates, have difficulties in wet stack emission applications, and generally do not provide accurate mass concentration measurements. Additionally, conventional light scattering methods to detect particulate concentration are relatively sensitive to detecting small changes in an amount of particulate. However, such a method does not provide overall accuracy. Accordingly, in itself, the conventional light scattering method is not very useful in detecting an amount of particulate mass present in an air sample, unless calibrated to the specific mass under current measurement without change of particle characteristics.

Embodiments herein differ with respect to conventional analyzer systems. For example, at least one embodiment herein is directed to one or more unique ways of calibrating an optical sensor for detecting a presence of particular matter in a fluid sample.

More specifically, one embodiment herein includes a system for monitoring a particulate matter in a fluid sample. The system can include a conduit, one or more optical sensors, and an analyzer. A fluid sample flow including particulate matter passes through the conduit. A concentration, distribution and/or characteristics of particulate in the fluid sample can change over time. The one or more optical sensors in the system monitor optical energy scattered from the particulate matter in the fluid sample flow as it passes through an illuminated section of the conduit. The illuminated section may be of a constant light source, pulsed light source, a varied light source, etc.

A magnitude of the optical energy sensed by the one or more optical sensors varies depending on particulate matter present in the fluid sample flow as it passes through the conduit. The analyzer analyzes the magnitude of the optical energy sensed by the one or more optical sensors. The analyzer detects a change in the optical energy.

In one embodiment, the change in the optical energy indicates a change in the particulate matter in the fluid sample flow. A change in the particulate matter can include a change in any parameter associated with the particulate matter such as size of the particulate matter, a change in refractive index of the particulate matter, etc. In response to detecting an event such as the change in the optical energy sensed by the one or more sensors, the analyzer initiates one or more functions such as calibration of the one or more optical sensors, diagnostic testing of the analyzer system, a purging of the system, etc.

As described herein, note that scattered optical energy can include optical energy that is reflected, diffracted, and/or refracted off of the particulate matter in the sample under test.

A specific event that triggers calibration, diagnostics, etc., can vary depending on the embodiment. For example, in further embodiments, the analyzer can monitor light (i.e., optical energy) scattering as sensed by each of multiple sensors. A first sensor can measure scattered optical energy at a primary angle relative to a direction of an incident light source while a second sensor can measure scattered optical energy at a secondary angle with respect to the incident light source.

In one embodiment, the analyzer repeatedly monitors a value or function such as ratio of light scattered by the first sensor and second sensor and generates the triggering event in response to detecting that the value or function changes over time while monitoring the fluid sample. The change in the value or function may indicate a condition such as that particulate matter in the fluid sample has changed, thus, triggering the event to recalibrate the first and/or second optical sensors.

In more specific embodiments, the change in the value such as above or beyond a threshold value can be indicative of a change in a mass concentration of the particulates in the fluid sample. Depending on the embodiment, the threshold can be an absolute change in value, a percent change in value, or a statistical change in value (e.g., coefficient of variation). In yet another embodiment, the change in the value can be indicative of a variation in a composition of the particulates in the fluid sample. In still another embodiment, the change in the value or function can be indicative of a variation in a size of the particulate in the fluid sample, and so on.

As discussed further below, embodiments herein can include a probe disposed in a flue to receive the fluid sample. As mentioned above, the fluid sample can include particulate matter to be monitored. The probe collects the fluid sample for transmission through a conduit. The system can include a dilution stage to dilute and condition the fluid sample with a dilution gas to a desired condition. The system also can include a heater to heat the diluted gas sample. In one embodiment, the probe, dilution stage, and/or heater are located in or near the flue.

The system as discussed herein can include a channel (e.g., a conduit, pipe, etc.) through which to convey the heated and/or diluted fluid sample for analysis by an analyzer that monitors scattered light or optical energy of particulate matter within an illuminated section of channel in the fluid sample to determine whether or not to calibrate or recalibrate one or more optical sensors.

Calibration of the system and/or optical sensors can include physically collecting particulate matter from the fluid sample at or around a time of detecting the triggering event. The collected particulate matter is then measured and used as a basis for calibrating the analyzer system and/or respective one or more optical sensors.

These and other more specific embodiments are disclosed in more detail below.

It is to be understood that the system, in addition to hardware, as discussed herein can include software to carry out embodiments as described herein.

As discussed above, techniques herein are well suited for use in particulate analyzer systems. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where appropriate, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION

Figure 1:
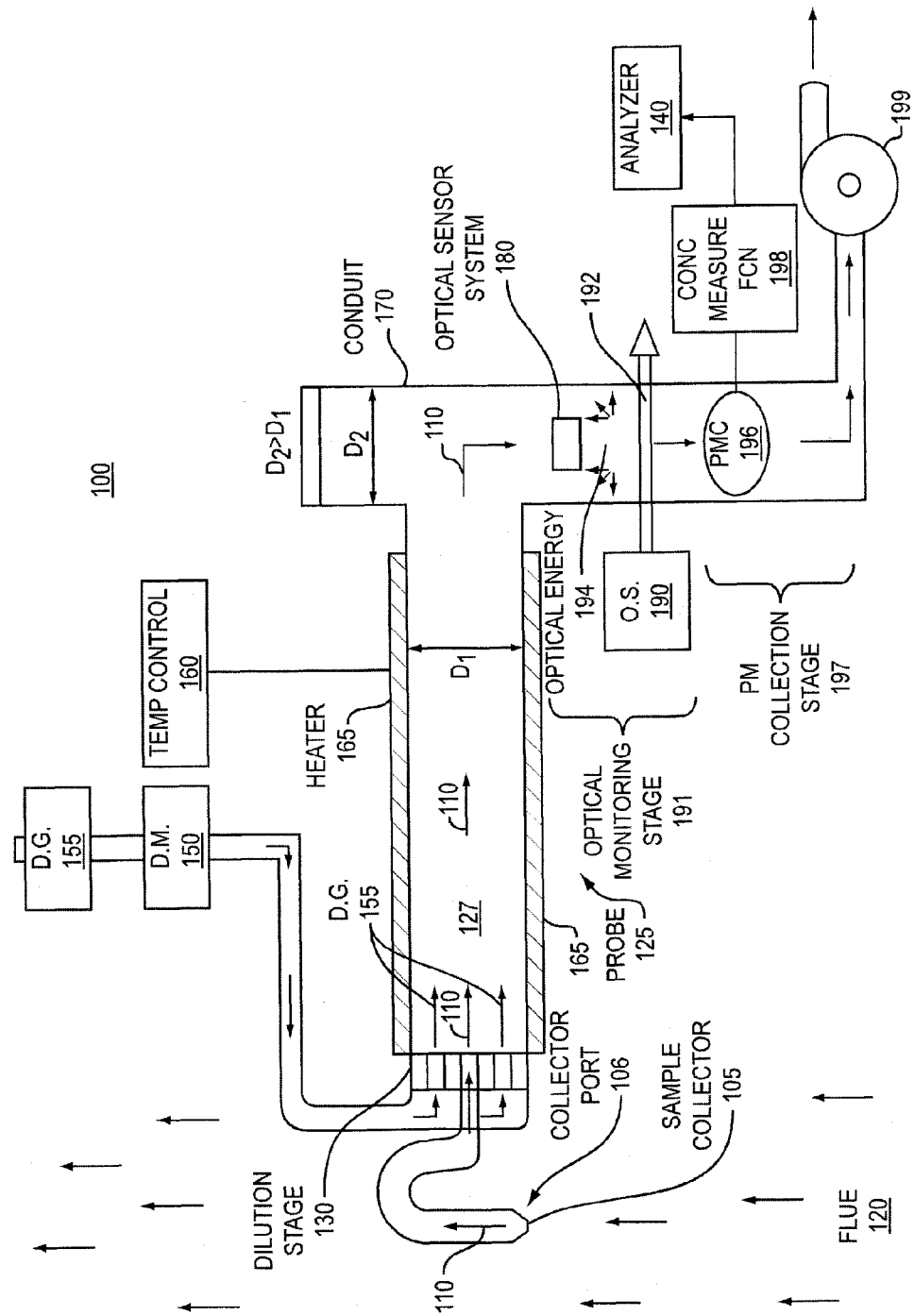
FIG. 1 is an example diagram of a system for analyzing presence of particulate matter in a fluid sample according to embodiments herein.

According to example configurations herein, a fluid sample including particulate matter passes through a conduit. One or more optical sensors monitor optical energy scattered off of the particulate matter in the fluid sample as it passes through an illumination beam within the conduit. A magnitude of the scattered optical energy sensed by the one or more optical sensors varies depending on particulate matter present in the fluid sample. An analyzer analyzes the magnitude of the scattered optical energy sensed by the one or more optical sensors and detects a change in the optical energy. The change in the magnitude of the detected, scattered optical energy can indicate a change in the particulate matter present in the fluid sample flow. In response to detecting a condition such as the change in a magnitude of the scattered optical energy, the analyzer initiates one or more functions such as calibration of the one or more sensors, purging the system with zero gas to check sensors, cleaning the system, execution of diagnostics, etc.

As will be discussed below in accordance with one embodiment, a particulate matter analyzer can include an optical source that generates a reference beam such as a polarized reference beam for directing through the fluid sample. The one or more optical sensors as mentioned above measure a portion of the optical energy that scatters off of particulate matter in the fluid sample.

In yet another embodiment, the optical source can emit two or more wavelengths that can add to the differentiation of measured scattered optical energy. The differentiation of the measured scattered optical energy can be correlated to changing characteristics of the aerosol.

In further embodiments, the scattered optical energy can be measured at one or more angles relative to the origin of the incident optical source, that can add to the differentiation of measured scattered optical energy. The differentiation of the measured scattered optical energy can be correlated to changing characteristics of the aerosol.

In another embodiment, the scattered optical energy can be measured at one or more angles relative to the origin of an incident optical source, which emits one or more wavelengths, which can add to the differentiation of measured scattered optical energy. The differentiation of the measured scattered optical energy can be correlated to changing characteristics of the aerosol.

In another embodiment, the orthogonal components of the scattered optical energy can be measured through polarizing media that are 90 degrees out of phase at one or more angles relative to the origin of an incident polarized optical source, which can add to the differentiation of measured scattered optical energy. The differentiation of the measured scattered optical energy can be correlated to changing characteristics of the aerosol.

In one embodiment, directly opposite the optical source resides a reference detector to receive the optical beam passing through the fluid sample. The reference detector measures the amount of incoming light and regulates the current provided to the optical energy source such as a light, laser diode, etc., such that a substantially constant amount of power is transmitted through the fluid sample for testing a presence of particulate matter.

In another embodiment, the amount of power emitted by the optical source may be monitored by a reference detector prior to the light beam striking the fluid sample, whereby the reference detector is at an angle not in direct alignment with the incident source. The reference detector measures the amount of incoming light and regulates the current provided to the optical energy source such as a light, laser diode, etc., such that a substantially constant amount of power is transmitted through the fluid sample for testing a presence of particulate matter.

In yet further embodiments, as discussed below, the optical sensors can be positioned to simultaneously (or at different times) measure a back-scattering component and forward-scattering component of the scattered optical energy. A function such as a ratio of the two scattering components may provide an indication such as a size of the particulate matter in the sample. Also, the aggregate intensity of scatterings detected by one or more sensors detecting scattered light is typically a function of the mass concentration of particulate matter in the sample.

Now, more specifically, FIG. 1 is an example diagram of a system 100 for analyzing fluid samples according to embodiments herein.

As shown, and by way of a non-limiting example, sample collector 105 can be a conduit or tube-like material having a collection port 106 for receiving a fluid sample 110 from a source such as flue 120. Sample collector 105 represents a portion of probe 125 for initially receiving a fluid sample 110. Sample collector 105 can be of a button-hook type or other suitable shape to facilitate the extraction of particles from fluid sample.

The fluid sample 110 can include particulate matter such as one or more by-products of combustion or some other origin.

As mentioned above, a presence of the particulate matter in the fluid sample can be monitored to detect attributes such as the mass, concentration, size, etc., of particulate matter in the fluid sample 110. The particulate matter present in the fluid sample 110 can vary in size and shape depending on a respective source producing the particulate matter. In one embodiment, the particulate matter in fluid sample is less than 20 micrometers in size although the concepts as described herein can be applied to particulate matter of generally any suitable size.

In addition to variations with respect to shape and size, the optical scattered and absorption properties of the particulate matter also can vary.

During operation of system 100, sample collector 105 of probe 125 provides a channel through which to transmit the collected fluid sample 110 into subsequent stages of probe 125 such as dilution stage 130. As its name suggests, the dilution stage 130 dilutes the fluid sample 110 received from the sample collector 105 and facilitates a flow of the fluid sample 110 to conduit 170. In one embodiment, the dilution stage dilutes the fluid sample 110 by an approximate range of 16:1 (e.g., sixteen parts of dilution gas to one part sample under test).

In the example embodiment as shown, the dilution module 150 inputs dilution gas 155 into the dilution stage 130 in order to dilute the received fluid sample 110 by a factor of, for example, 16:1. That is, the dilution stage dilutes 1 part of the fluid sample 110 with 16 parts of dilution gas 155. Dilution gas 155 can be any suitable type of gas such as air, etc., The dilution gas may be pre-dried prior to using it to dilute the fluid sample 110.

Diluting the fluid sample 110 with dilution gas 155 can simulate the environmental conditions exposing the fluid sample 110 and respective particulate matter to the open atmosphere such as at the output of the flue 120. Thus, the fluid sample 110 can be analyzed to determine attributes of particulate matter being outputted from the flue into open atmosphere at the top of a stack even though the fluid sample 110 being tested travels through probe 125 and is never exposed to open atmosphere before being tested via system 100.

In addition to diluting the fluid sample 110, the dilution gas 155 (e.g., scrubbed air) can have an effect of drying below a relative humidity threshold value and cooling the received fluid sample 110.

Figure 2:
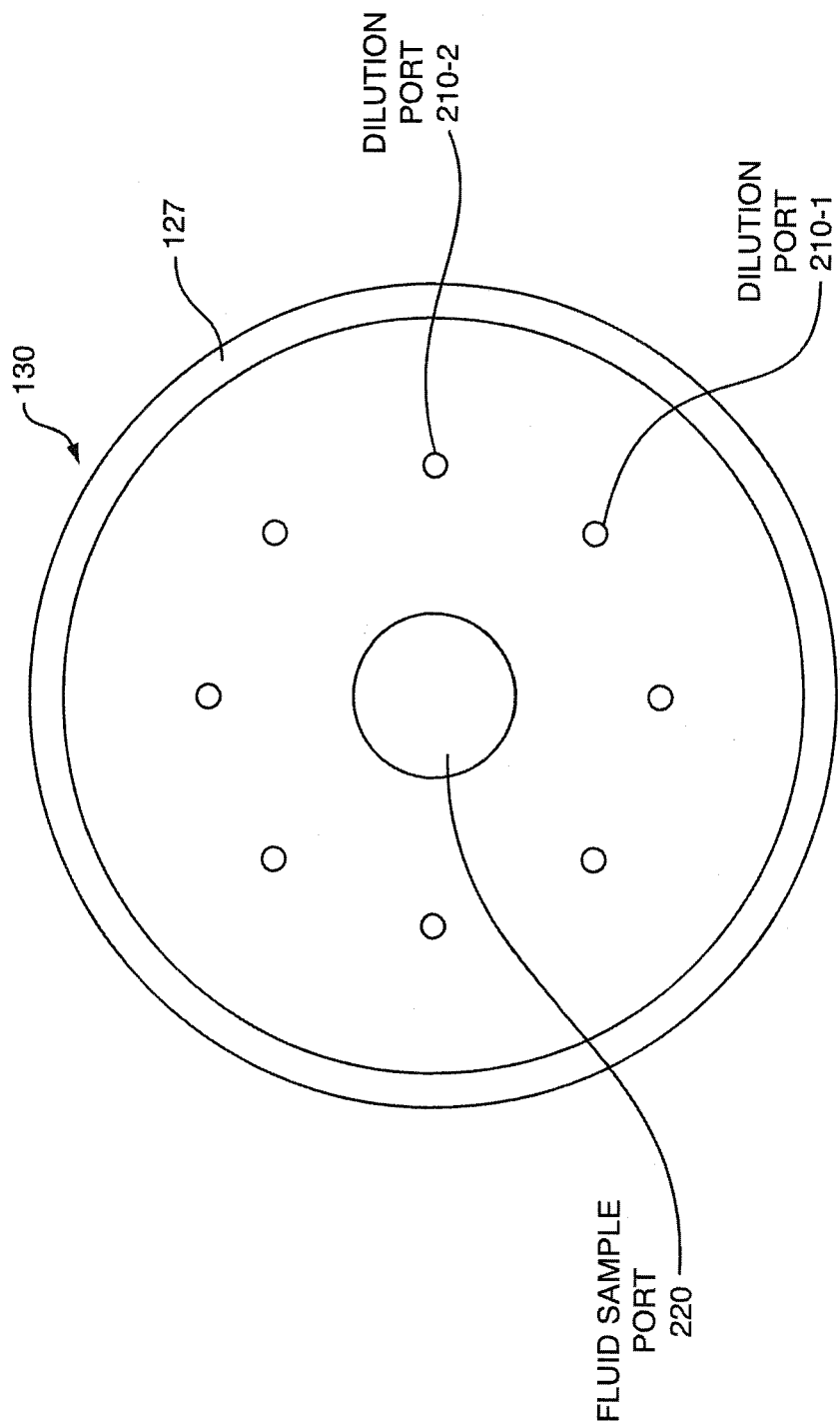
FIG. 2 is an example diagram illustrating cross section of a dilution stage according to embodiments herein.

FIG. 2 is an example diagram illustrating a cross-sectional view of dilution stage 130 according to embodiments herein. As shown, the fluid sample 110 passes through fluid sample port 220 into a subsequent stage of probe 125 heated by heater 165. Dilution gas 155 passes through dilution ports 210 (e.g., dilution port 210-1, dilution port 210-2, dilution port 210-3, etc.) into the subsequent stage of probe 125. The fluid sample 110 and the dilution gas 155 pass through dilution stage 130 in the same direction into the conduit 127 of, probe 125. Fluid sample port 220 can be positioned at or near a center of the dilution stage 130 while dilution ports 210 are distributed around the fluid sample port 220 to reduce a likelihood that particulate matter in the fluid sample 110 will be deposited on the walls of conduit 127 as it passes through probe 125.

In one embodiment, the dilution module 150 controls a velocity of the dilution gas 155 into the conduit 127 to be approximately equal to a velocity of the fluid sample 110 to prevent or reduce turbulence with respect to the fluid sample 110. In one embodiment, the velocity of the diluted fluid sample is approximately 20-120 feet per second although the velocity can fall outside this range depending on the embodiment.

Referring again to FIG. 1, system 100 can include a temperature controller 160 and a respective heater 165. The temperature controller 160 can control the respective heater to heat the gas in the probe 125 to a temperature such as between 50 and −180 degrees Celsius, although the gas in the probe can be heated to any suitable temperature in different embodiments. Applying heat via heater 165 can help to reduce an amount of particulate matter deposited on the walls of probe 125 through a so-called thermophoretic effect.

By way of a non-limiting example, the diameter of the probe 125 (e.g., a conduit, pipe, etc.) can be around 0.5 inches. However, the diameter can vary depending on the embodiment.

In one embodiment, the diluted fluid sample 110 in probe 125 can flow at a rate of approximately 6 to 8 meters per second, although this rate can vary depending on the application. The diameter D2 of the conduit 170 can be approximately 2 inches. Again, these diameter values can vary depending on the embodiment.

Exhaust device 199 can be configured to provide suction to draw the diluted fluid sample 110 through the probe 125 and respective conduit 170.

The conduit 127 can be configured to have a diameter D1. Conduit 170 can be configured to have a diameter D2, which is substantially larger than the diameter D1. The larger diameter of the conduit 170 has an effect of reducing a speed of the particulate matter when it passes from conduit 127 into conduit 170. Reducing a velocity of the particulate matter in the diluted fluid sample 110 reduces a likelihood that the particulate matter will be deposited on or stick to inner walls of the conduit 170 through which the fluid sample 110 passes.

It should be noted that parameters such as a length, diameter, etc., of the sample collector 105, probe 125, conduit 170, etc., can vary depending on the application. However, as briefly mentioned above, the parameters of system 100 are controlled such that the fluid sample 110 being tested at later stages (e.g., optical sensor 180) of the conduit 170 simulates the particulate matter discharged from the flue 120. In other words, the system according to embodiments herein has an effect of "aging" the fluid sample 110 for subsequent optical testing by optical monitoring stage 191. The "aged" fluid sample 110 simulates the environmental conditions as if the flue gas were exposed to open atmosphere for a certain amount of time. Accordingly, fluid sample 110 in the conduit 170 can have similar characteristics as the particulate matter outputted from flue 120 into the atmosphere.

Parameters of the system 100 can be adjusted to increase or decrease a residence time of particulate matter traveling through probe 125 and conduit 170 for testing at optical monitoring stage 191. Accordingly, system 100 can be designed to provide different residence times depending on the type of particulate matter being tested.

To facilitate monitoring of the fluid sample 110, system 100 includes optical monitoring stage 191. Optical monitoring stage 191 includes an optical source 190 (e.g., laser, diode, etc.) and optical sensor system 180.

Optical source 190 generates optical beam 192 for directing through an aperture (e.g., window) of the conduit 170 and fluid sample 110. As the fluid sample 110 passes through the conduit 170 towards exhaust device 199, a portion of the optical beam 192 is scattered off of the particulate matter in the fluid sample 110 as optical energy 194.

Figure 3:
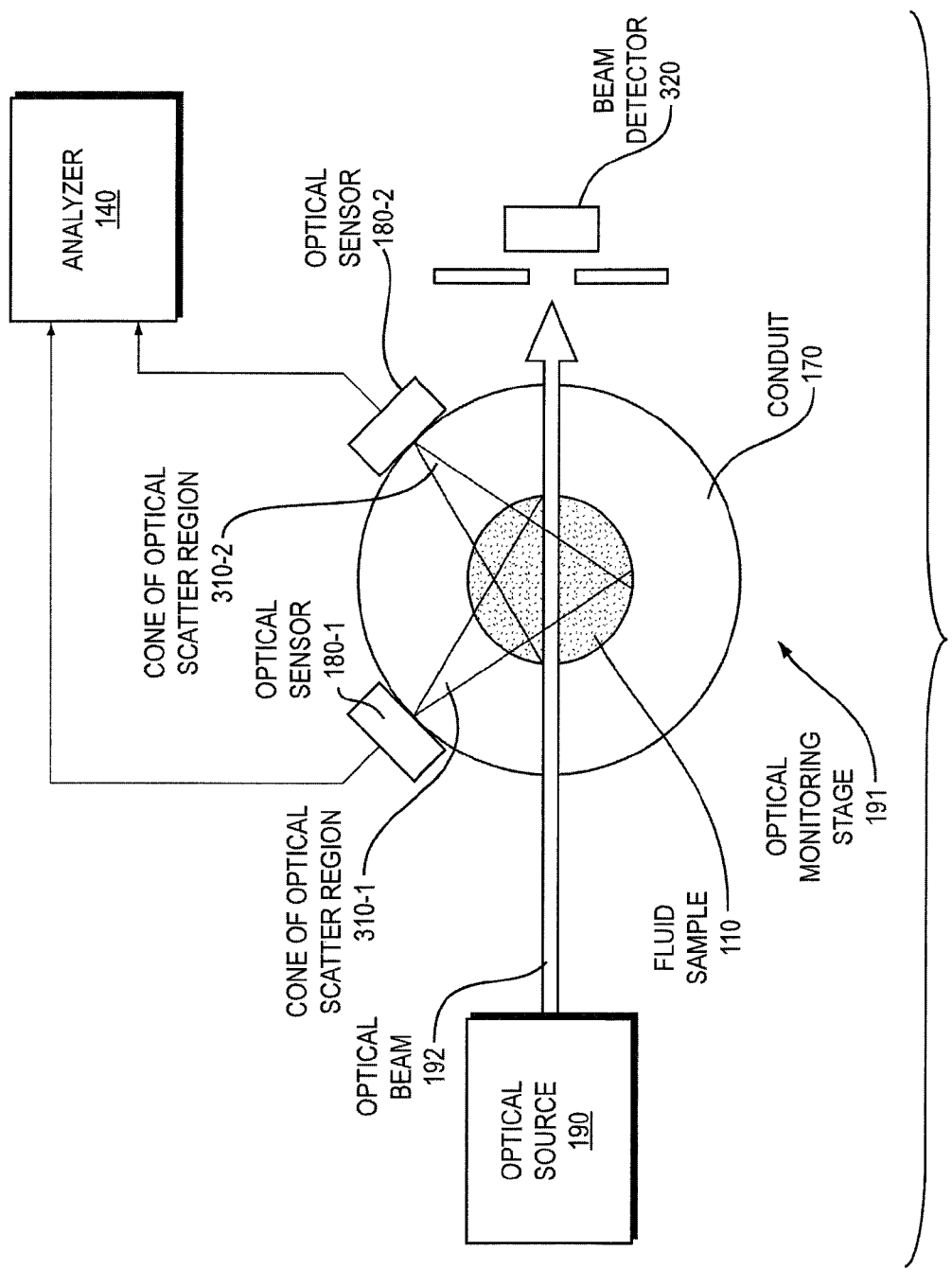
FIG. 3 is an example diagram illustrating one or more sensors for measuring optical energy scattered off of particulate matter in a fluid sample according to embodiments herein.

In one embodiment, it is possible to measure the intensity of the optical beam 192 with a beam detector 320 (FIG. 3). The beam detector 320 may or may not be positioned directly opposite of the optical source 190.

Optical sensor system 180 (e.g., one or more optical sensors) receives the optical energy 194 scattered off of particulate matter and produces an output indicative of a magnitude of the detected optical energy 194. As previously discussed, the optical energy 194 can include optical energy from the optical beam 192 reflecting off particulate matter in the fluid sample 110, optical energy from the optical beam 192 refracting off of particulate matter in the fluid sample 110, optical energy from the optical beam 192 diffracting off of particulate matter in the fluid sample 110, etc.

FIG. 3 is an example detailed diagram illustrating a cross-sectional view of the optical monitoring stage 191 in conduit 170 according to embodiments herein. In general, this cross-sectional view illustrates passing of the optical beam 192 through the fluid sample 115 and detection of optical energy from the optical beam 192 scattered off the sample to the sensors 180.

During operation, optical source 190 generates optical beam 192 through a transparent window of conduit 170. Typically, a percentage of the optical beam 192 passes through the fluid sample 110 and strikes beam detector 320. As previously discussed, a portion of the optical beam 192 scatters off the sample towards sensors 180.

In one embodiment, beam detector 320 generates a signal that is fed back to the optical source 190. By way of a non-limiting example, the optical source 190 utilizes the feedback signal received from the beam detector 320 to maintain a power output of the optical beam 192 to a substantially constant value within approximately 0.2-10 milliwatts.

Additionally, as shown in this example embodiment, the optical sensors 180 can include optical sensor 180-1 and optical sensor 180-2. Optical sensor 180-1 detects a portion of energy from the optical source beam 192 that scatters off of the particulate matter in the fluid sample 110 within cone of optical sensing region 310-1. Optical sensor 180-2 detects a portion of energy from the optical source beam 192 that scatters off of the particulate matter in the fluid sample 110 within cone of optical sensing region 310-2.

Thus, in accordance with one example embodiment, optical sensor 180-1 detects backward scattering optical energy off particulate matter in the fluid sample 110. Optical sensor 180-2 detects forward scattering optical energy off particulate matter in the fluid sample 110.

By way of a non-limiting example, the forward scattering angle range of detection by optical sensor 180-2 extends from about 10° to 50° relative to an axis of the optical source beam 192; the corresponding backscatter angle detected by optical sensor 180-1 can be in a range of between 120° to 170° with respect to the optical beam 192. However, note that any suitable range of scattering angles can be detected in accordance with embodiments herein.

In an example embodiment, a flow of gas such as clean air can be fed over the primary optical surfaces exposed to particle flow, in order to protect them from particle deposition, and to cool the active components of the system. Also, in certain embodiments, it may be useful to heat the photometric assembly. The illumination beam, and photodetector signals can be carried through a fiber optic cable, thereby allowing any temperature sensitive components to reside within a temperature controlled housing.

As previously discussed, the magnitude of the optical energy 194 scattering off particulate matter varies depending on a mass concentration of particulate matter in the fluid sample 110 passing through the optical beam 192 generated by optical sensor 190.

Referring again to FIG. 1, system 100 includes analyzer 140. Analyzer 140 receives magnitude information generated by detectors 180-1 and 180-2. Analyzer 140 can be configured to monitor the magnitude of energy scattered off of particulate matter in the fluid sample 110 to calculate, for example, a mass concentration of the particulate matter in the fluid sample over time.

In one embodiment, the optical sensor system 180 produces one or more real-time electrical signals that vary depending on an amount of detected scattered optical energy 194. The optical sensor system 180 can be highly sensitive to detecting small changes in the amount of scattered light. Such an embodiment is therefore well-suited for detecting conditions such as changes in particulate matter.

Of course, a mass concentration of the particulate matter can change over time depending on a source producing the particulate matter. As the mass concentration or other attribute of particulate matter in the monitored fluid changes over time, the magnitude of the detected optical energy 194 changes over time as well. Accordingly, the analyzer 140 can identify when there is a change with respect to the particulate matter based on the magnitude of detected optical energy 194 as sensed by one or more sensors in optical sensor system 180.

In one embodiment, the analyzer 140 utilizes the magnitude information received from the optical sensor system 180 and applies one or more corresponding correction factors to generate a mass concentration value representing an amount of particulate matter in the fluid sample 110. Thus, it is possible to use optical sensors 180 as described herein to detect when changes in particulate matter occur as well as detect a mass concentration of particulate matter in a fluid sample. A dilution rate and flow rate of the diluted fluid sample is known and are used in conjunction with the detected mass concentration to calculate an amount of particulate matter in the fluid sample 110.

As discussed below, the one or more corresponding correction factors for generating a particulate matter concentration can be derived based on calibration of the optical sensor system 180 using particulate matter collection stage 197.

In general, particulate matter collection stage 197 and, more specifically, particulate matter collector 196 enables collection of particulate matter for physically measuring a mass concentration of particulate matter in the fluid sample 110.

Generation of a mass concentration of particulate matter in the fluid sample 110 based only on information received from the optical sensor system 180 may be inaccurate. In other words, optical sensor system including sensors 180 may need to be calibrated at certain times to provide more accurate readings. To calibrate the optical sensor system 180 at optical monitoring stage 191, system 100 can include particulate matter collection stage 197.

In one embodiment, the particulate matter collection stage 197 produces an accurate measurement of particulate matter in the fluid sample 110 via steps of physically collecting the particulate matter in fluid sample 110 and subsequently measuring a mass of the collected particulate matter from the fluid sample 110.

In one embodiment, use of the particulate matter collector 196 enables true mass concentration measurement and therefore requires no mass calibration in the field while enabling continuous mass referencing for the optical monitoring stage 191.

In one embodiment, the particulate matter collector 196 is a filter configured to collect the particulate matter from the fluid sample 110. When positioned in the path of the fluid sample 110, a mass of the filter changes depending on a mass of collected particulate matter. As an example, the analyzer 140 can include an inertial microbalance assembly to measure a frequency of oscillation of the particulate matter collector 196 that is then used to determine a mass concentration of collected particulate matter.

One potential drawback of using the particulate matter collector 196 (e.g., filter) is related to particle loading onto a respective filter media. Once saturation of particulate matter on the filter is reached, the filter requires maintenance. That is, the filter may need to be replaced with a new filter or cleaned to remove previously collected particulate matter. Analyzer 140 can control when the particulate matter collector 196 is used to collect particulate matter in the fluid sample 110 in order to calibrate the one or more sensors in the optical monitoring stage 191.

In both ambient and source emission type monitoring applications, it may be desirable to reduce a need for servicing system 100 and replacement or cleaning of particulate matter collector 196. As discussed below, use of a time proportioned sampling of the particulate matter collector 196 can reduce service requirements. When not in use, the particulate matter collector 196 does not collect the particulate matter in the fluid sample 110.

In one embodiment, analyzer 140 of system 100 calculates a value based on a function such as a ratio of forward scattered optical energy to the actual mass concentration as detected by particulate matter collection stage 197. Analyzer 140 also can be configured to keep track of a ratio of forward scattered optical energy to backward scattered optical energy to determine when there is a change with respect to characteristics of the particulate matter in the fluid sample 110.

In an example embodiment, the actual mass concentration can be taken from the last 5 minutes of a 15-minute time proportioned mass measurement. An average of the forward scattering signal can be taken from the same averaging period. By plotting or keeping track of a value the mass correction factor (F:T) against the function such as ratio of scattering signals (f{F,B}), it is possible to establish a relationship of mass correction as a function of the scattering signals.

A correction factor can be calculated as function of the forward to back scattering ratio. For example, a mass adjustment or correction factor can be calculated based on a relationship of forward and back scattering. In one embodiment, the mass adjustment or correction factor can be multiplied by the forward scattering signal to produce a mass concentration value for the fluid sample 110.

This calibration curve can be performed continuously in real-time. Should any changes in stack conditions change due to varying fuel types, or other reasons, the most recent calibration curve could be applied to the real-time optical signal.

Figure 4:
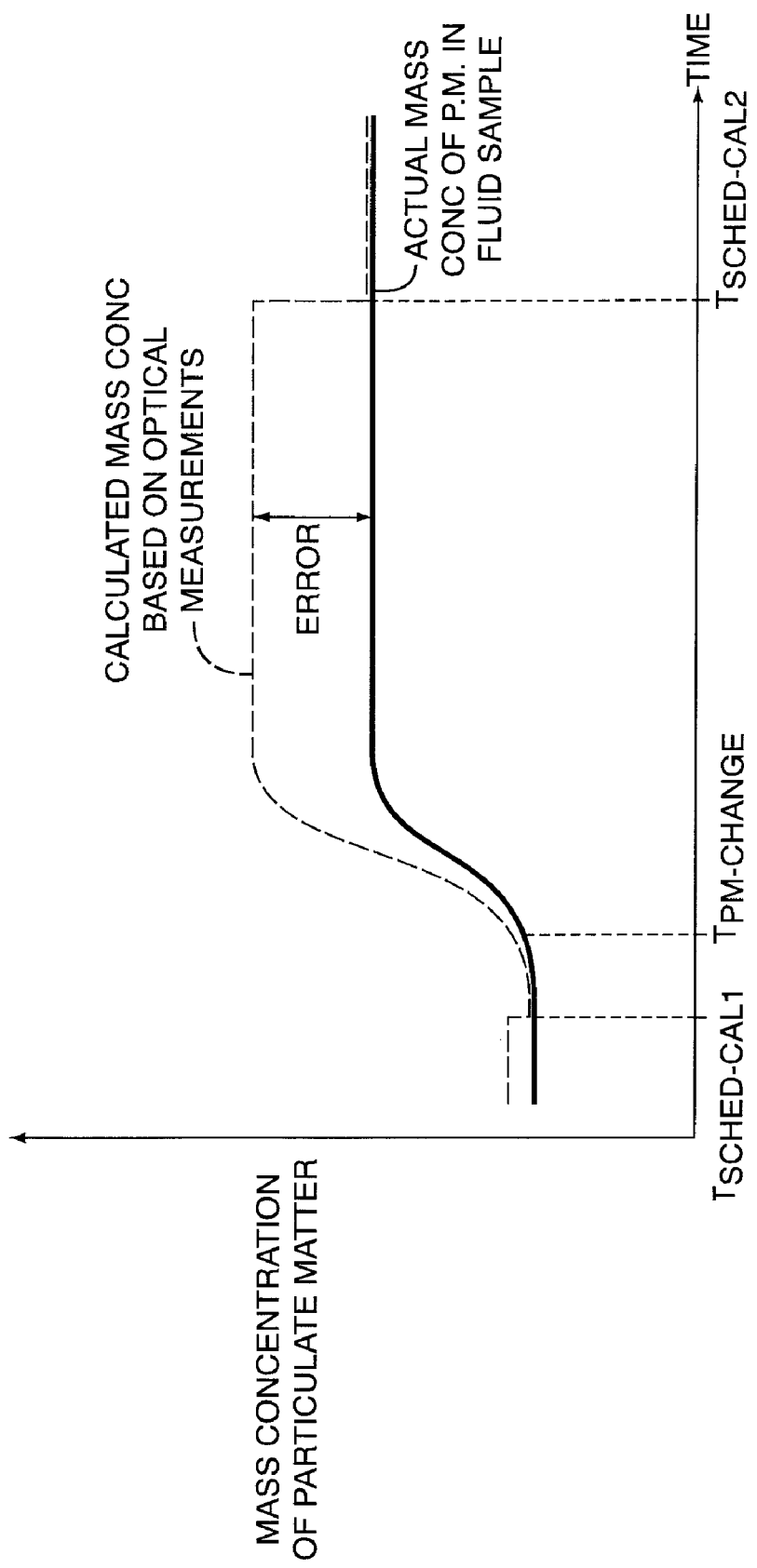
FIG. 4 is an example graph illustrating the inaccuracy of optically measuring particulate matter in a fluid sample according to conventional methods.

FIG. 4 is an example theoretical graph illustrating inaccuracy of using an optical system to measure particulate matter according to conventional methods.

Graph 400 illustrates a sequence of calculated mass concentration values generated based on information received from the optical monitoring stage 191 versus the actual mass concentration of particulate matter in a fluid sample 110. Via repeated sampling, an operator can be apprised of an amount of particulate matter in the fluid sample 110 at any instant in time.

At times of scheduled calibrations, the calculated mass concentration value for the fluid sample 110 derived from optical monitoring stage 191 can be quite accurate. For example, note that an accuracy of detecting a mass concentration of the particulate matter using optical monitoring is accurate just after calibration of the optical monitoring stage 191 at times $T_{SCHED\_CAL1}$ and $T_{SCHED\_CAL2}$. As previously discussed, the optical monitoring stage 191 can be calibrated at scheduled times via collecting particulate matter via particulate matter collector 196 and using the detected mass concentration to calibrate optical monitoring stage 191.

However, as discussed herein, the optical monitoring stage 191 can become inaccurate as a result of a change in characteristics of the particulate, matter being detected in fluid sample 110. For example, at time $T_{PM-CHANGE}$, the concentration of the particulate matter in the fluid sample 110 changes. The calculated mass concentration of particulate matter as derived from optical monitoring becomes inaccurate as a result of the change in attributes of the particulate matter. Although, the calculated mass concentration becomes inaccurate at time $T_{PM-CHANGE}$, eventually, the calculated mass concentration values generated based on the optical monitoring stage 191 becomes more accurate at scheduled calibration at time $T_{SCHED\_CAL2}$. In other words, calibration at scheduled time $T_{SCHED\_CAL2}$ results in subsequent accurate mass readings.

Note that scheduling of calibration times is shown by way of non-limiting example only and that the system 100 can be configured to initiate a respective recalibration via physical measuring of particulate matter in response to detecting a change in detected optical energy 194. In one embodiment, the system 100 can ensure that the sensors are calibrated every so often. For example, system 100 can keep track of a most recent time of calibrating the sensors 180. If the time since calibrating the sensors exceeds a threshold value, the system 100 can initiate recalibration even though there has been no significant change to the detected particulate matter present in the fluid sample.

Figure 5:
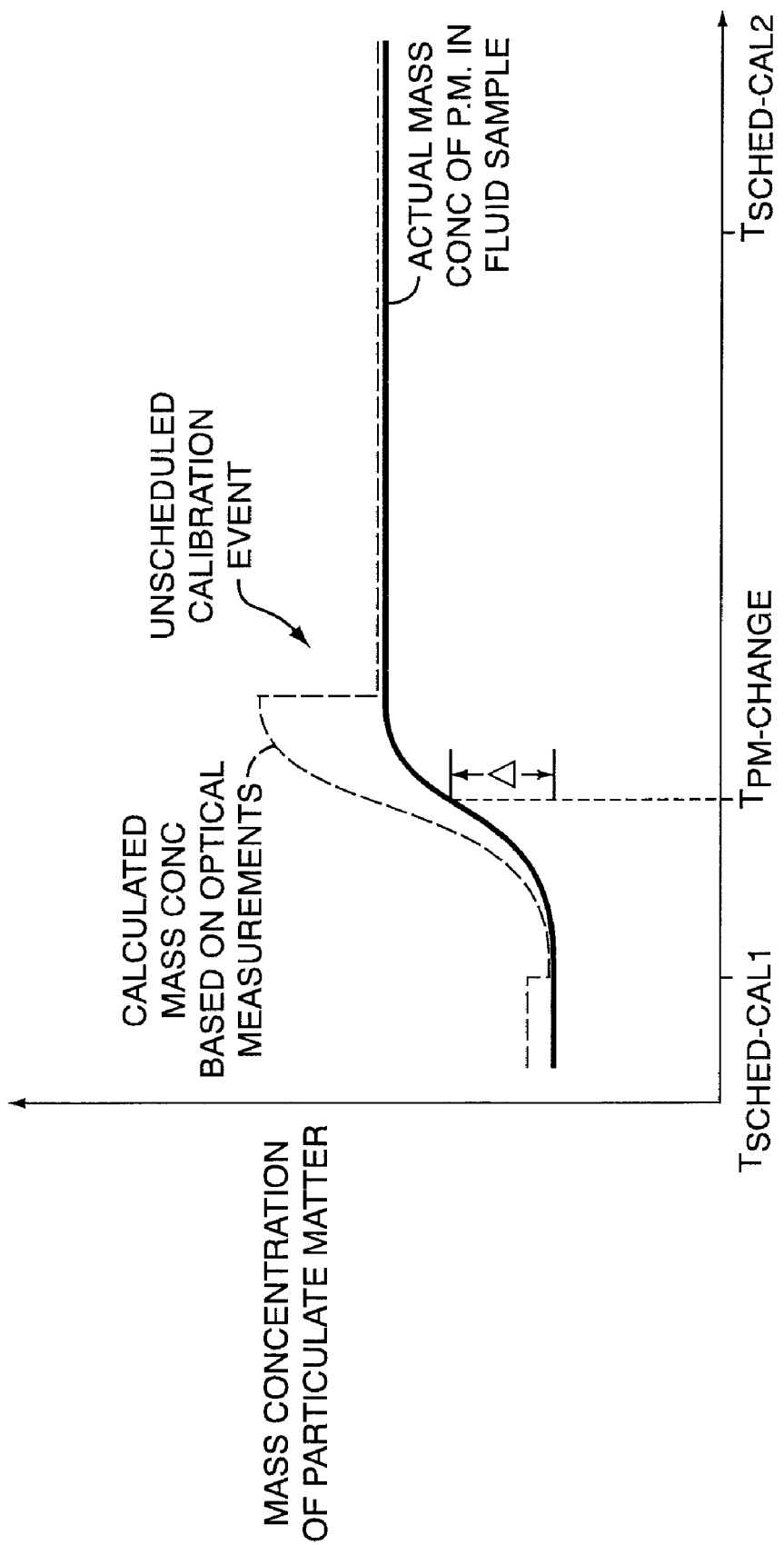
FIG. 5 is an example graph illustrating calibration of an optical monitoring stage according to embodiments herein.

FIG. 5 is an example theoretical graph illustrating calibration of the optical monitoring stage 191 according to embodiments herein. As shown, the optical monitoring stage 191 can be calibrated at prescheduled times, $T_{SCHED\_CAL1}$ and $T_{SCHED\_CAL2}$ based on physical measurements of the particulate matter collected form the fluid sample. However, in response to detecting a perturbation in the mass concentration in the fluid sample 110 as detected by optical monitoring stage 191, embodiments herein include initiating a supplemental physical collection of particulate matter in the fluid sample and calibration of the optical monitoring stage 191 at an unscheduled time at or around a time of detecting the change in magnitude of a scattered optical energy. The supplemental physical calibration can include collecting particulate matter from the fluid sample and then deriving a value indicative of a mass of matter in the sample. In one embodiment, the system 100 initiates an inertial mass measurement of particular matter in the fluid sample to calibrate the sensors.

In other words, when a magnitude of the scattering optical energy sensed by optical sensor system 180 changes more than a threshold amount, the analyzer 140 initiates calibration of the optical monitoring stage 191 via an accurate physical measurement of a mass concentration of particulate matter the fluid sample 110 (via collection) and then using the supplemental measurement at $T_{PM-CHANGE}$ to calibrate the optical monitoring stage 191 as shown.

In one embodiment, the particulate matter collector 196 and particulate matter collection stage 197 can be configured to physically collect the particulate matter less often than conventional methods based on the supplemental calibrations as discussed herein. For example, calibration or other functions associated with system 100 such as physical collection of particulate matter can be initiated when they are more useful such as when there are changes in the particulate matter in the fluid sample 110 (as measured by the detected optical energy 194) as opposed to implementing shorter intervals of scheduled calibration time.

As previously discussed, by way of a non-limiting example, an unscheduled physical recalibration at or around time $T_{PM\text{-}CHANGE}$ can be triggered by an event such as detecting a change in a value calculated based on tracking a function such as a ratio of back-scattered optical energy to a forward-scattered optical energy off of particulate matter in fluid sample 110.

In addition to calibrating the optical monitoring stage 191, note that the analyzer 140 can store calibration information in a repository. The calibration information can include: i) a calculated mass of the particulate matter, and ii) attributes of the change in magnitude of the optical scattering signal causing calibration of the optical monitoring stage 191. According to embodiments herein, in response to detecting a subsequent change in the magnitude of scattered optical energy (e.g., optical energy 194) that is similar to a previous change in optical scattering energy (that resulted in calibration using results from the particulate matter collection stage 197), embodiments herein include retrieving the stored calibration information for the previous calibration to calibrate the optical sensor in lieu of collecting the particulate matter from the fluid sample 110 to calibrate the optical sensor.

After a relationship of this asymmetric factor (i.e., the asymmetry between light scattered in the forward and backward directions by a particle or assemblage of particles) is established in comparison to the mass measurement, the service interval (e.g., the time different between scheduled calibrations) may be extended even more because stored information can be used to calibrate the optical monitoring stage 191 rather than require additional calibration using the particulate matter collection stage 197.

The embodiments as described herein are improvement over known methods such as those as discussed in U.S. Pat. No. 7,111,496, the entire teachings of which are incorporated herein by this reference. The original patent only assumes that moisture (relative humidity) may be reduced by use of heat. However, for applications that would require such a heat increase to reduce the relative humidity—this may bring the temperature well above the operating range of sensitive electronics. Via use of dilution drying of a sample with dry scrubbed air, the relative humidity can be controlled below a threshold.

Sensing of scattered optical energy in multiple directions as described herein provides additional information about changing characteristics of the particles being sampled and the asymmetric factor acts as a fingerprint from which a mass correction factor can be chosen. This unique approach reduces a need to use an inaccurate, aged calibration factor to calculate a mass concentration using optical input. After creating a library of asymmetric factors and corresponding mass calibration factors for multiple calibrations, embodiments herein can utilize the library of past calibrations to produce accurate concentration values for the fluid sample 110 instead of having to recalibrate the optical monitoring stage 191 when there is a change in scattered optical energy.

Also, embodiments herein enhance the above referenced patent and permits it full use in both ambient and source emissions applications.

Figure 6:
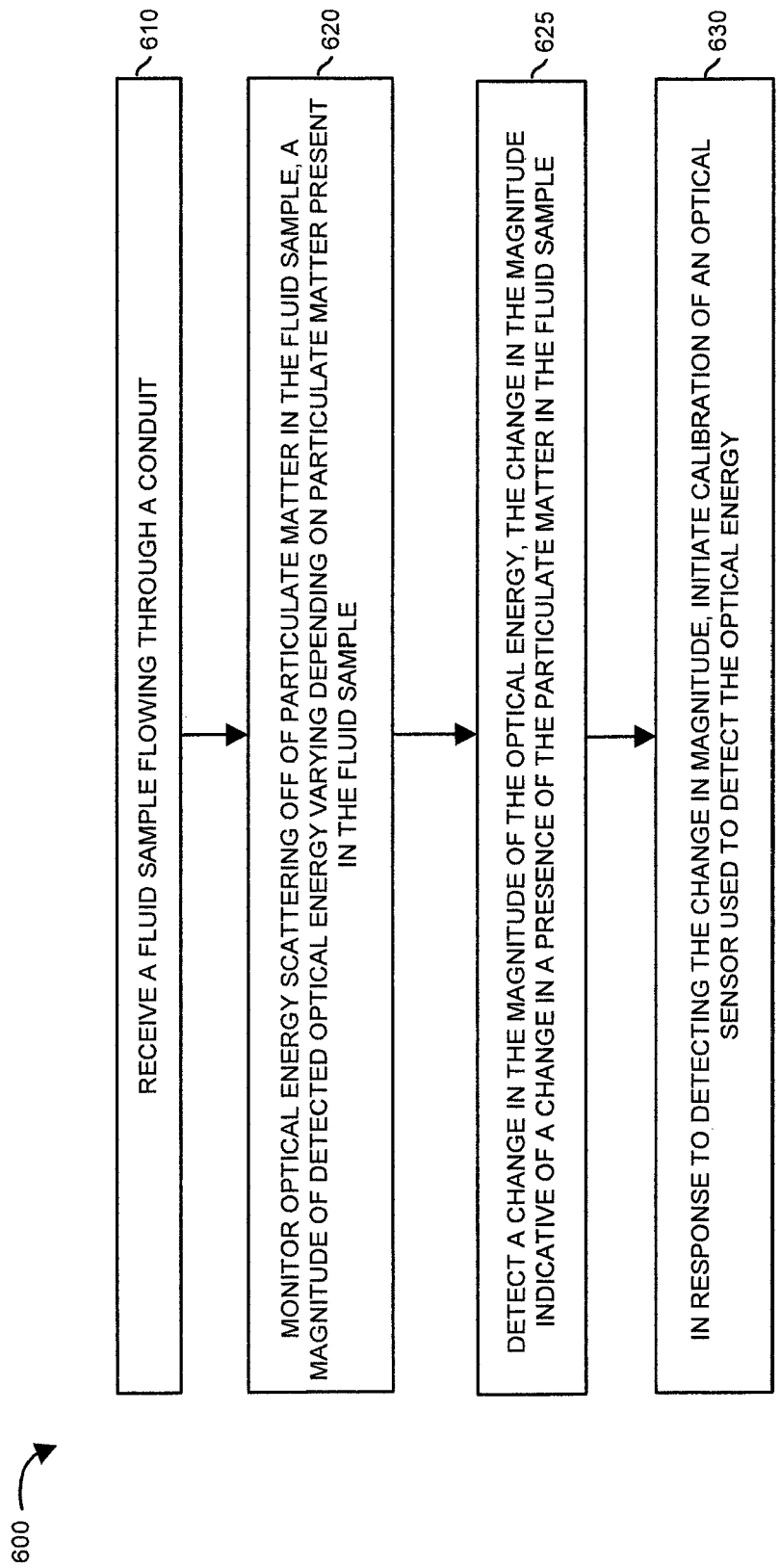
FIGS. 6-11 are example diagrams illustrating various methods according to embodiments herein.

FIG. 6 is a flowchart 600 illustrating a method according to embodiments herein. Note that there will be some overlap with respect to concepts discussed above for FIGS. 1 through 5.

In step 610, the analyzer 140 receives a fluid sample 110 flowing through conduit 170.

In step 620, the analyzer 140 monitors optical energy 194. The optical energy 194 detected by sensors 180 can include a portion of the optical beam 192 scattering off particulate matter in the fluid sample 110. A magnitude of the optical energy 194 varies depending on particulate matter present in the fluid sample 110.

In step 630, the analyzer 140 detects a change in the magnitude of the optical energy 194 detected by one or more sensors 180 in optical monitoring stage 191. The change in the magnitude is indicative of a change in attributes of the particulate matter in the fluid sample 110.

In step 640, in response to detecting the change in magnitude of the optical energy 194, the analyzer 140 initiates calibration of an optical sensor and/or optical monitoring stage 191 that is used to detect the optical energy scattering off of the particulate matter in the sample.

Figure 7:
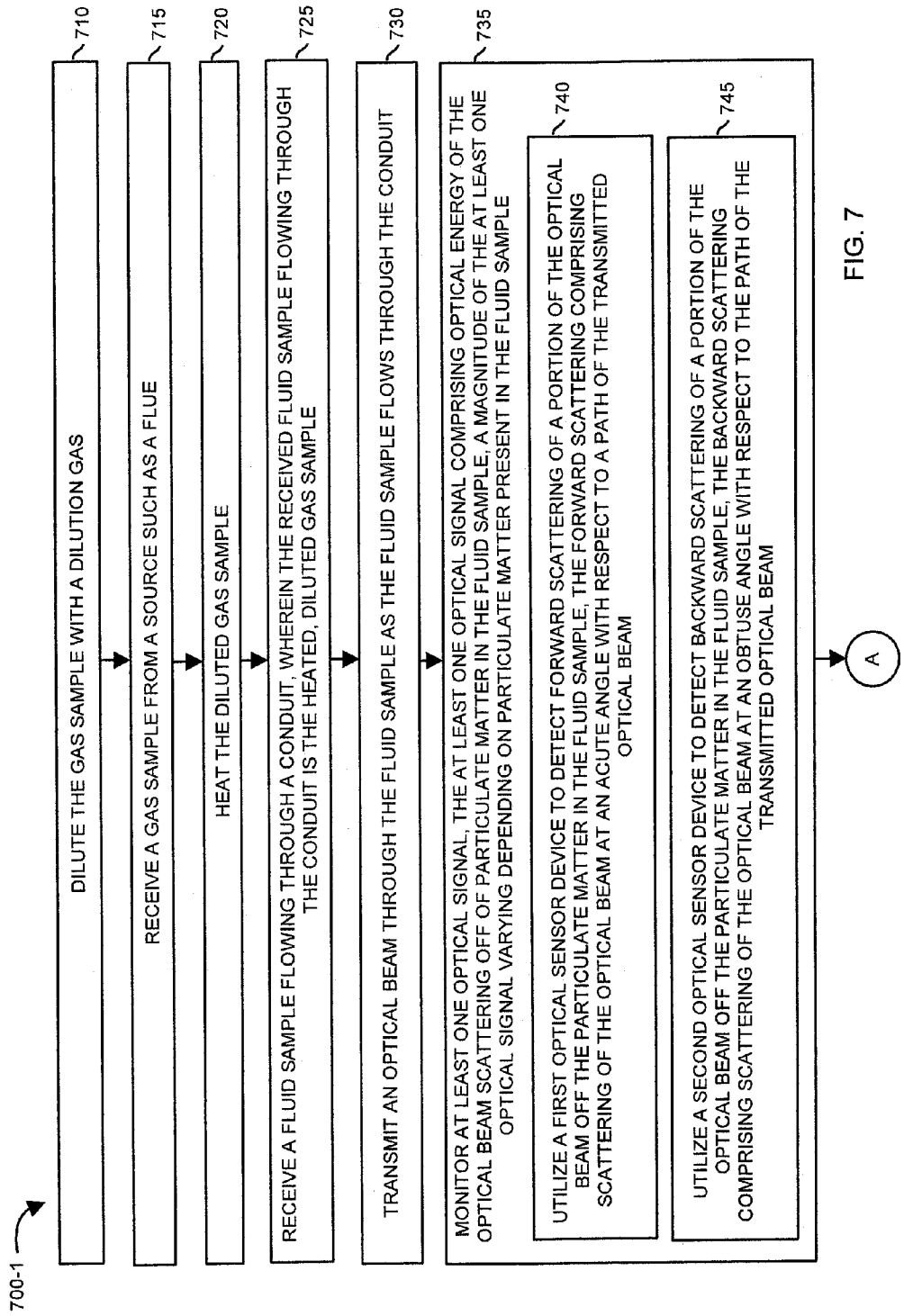
Figure 8:
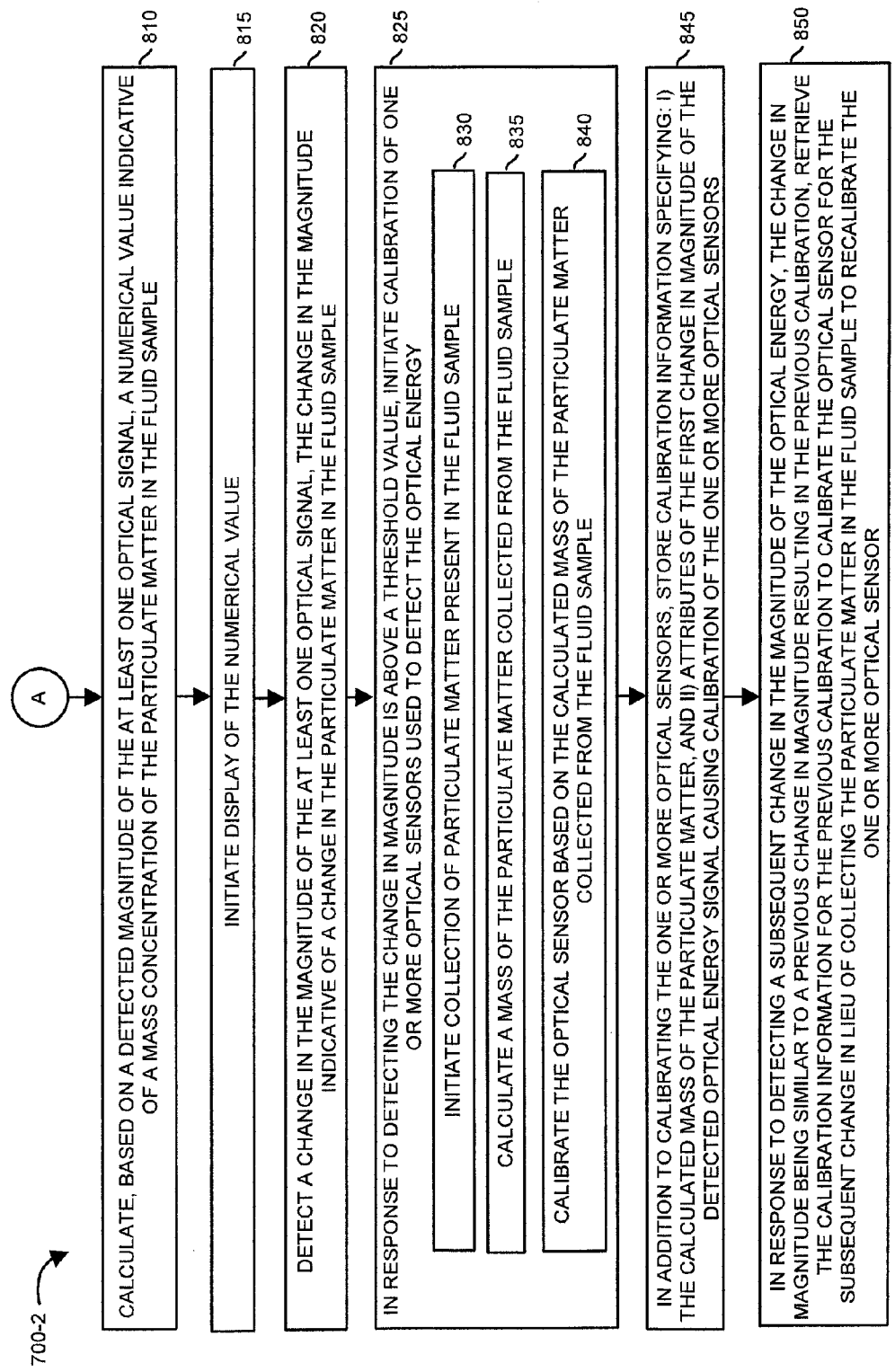

FIGS. 7 and 8 combine to form a flowchart 700 (e.g., flowchart 700-1 and flowchart 700-2) illustrating a method according to embodiments herein. Note that there will be some overlap with respect to concepts discussed above.

In step 710, system 100 receives a gas sample from a source such as a flue 120.

In step 715, dilution stage 130 of probe 125 dilutes the gas sample with a dilution gas 155.

In step 720, system 100 controls a temperature of the diluted gas sample. This can include heating and/or the fluid sample.

In step 725, the analyzer 140 receives a fluid sample 110 flowing through conduit 170. The received fluid sample 110 is the heated, diluted gas sample passed through conduit 127.

In step 730, the optical source 190 transmits an optical beam 192 through the fluid sample 110 as the fluid sample 110 flows through the conduit 170.

In step 735, the analyzer 140 monitors an optical energy 194. Optical energy 194 represents a portion of the optical beam 192 that scatters off of particulate matter in the monitored sample. A magnitude of the optical energy 194 varies depending on particulate matter present in the fluid sample 110.

In step 740, system 100 utilizes optical sensor device 180-1 to detect forward scattering optical energy 194. In one embodiment, the forward scattering comprises optical energy 194 scattered off of the particulate matter at an acute angle with respect to a path of the transmitted optical beam 192.

In step 745, system 100 utilizes optical sensor device 180-2 to detect backward scattering signals of the optical beam 192 off the particulates in the fluid sample 110. The backward scattering comprises scattering of the optical beam 192 at an obtuse angle with respect to a path of the transmitted optical beam 192.

In step 810, the analyzer 140 calculates, based on magnitude of the one or more optical scattering signals as detected by optical sensors 180-1 and 180-2, a numerical value indicative of a mass concentration of the particulate matter in the fluid sample 110.

In step 815, the analyzer 140 initiates display of the numerical value.

In step 820, the analyzer 140 detects a change in the magnitude of the optical energy 194 at one or more sensors. The change in the magnitude is indicative of a change in the particulate matter in the fluid sample 110.

In step 825, in response to detecting that the change in magnitude is above a threshold value, system 100 initiates calibration of one or more optical sensors such as sensors 180-1 and 180-2 in the optical monitoring stage 191.

In step 830, via particulate matter collection stage 197, the analyzer 140 initiates collection of particulate matter present in the fluid sample 110.

In step 835, the analyzer 140 calculates a mass of the particulate matter collected from the fluid sample 110.

In step 840, the analyzer 140 calibrates the optical sensor and/or optical monitoring stage 191 based on the calculated mass of the particulate matter collected from the fluid sample 110 at the particulate matter collection stage 197.

In step 845, in addition to calibrating the one or more optical sensors and/or optical monitoring stage 191, the analyzer 140 stores calibration information. The calibration information specifies: i) the calculated mass of the particulate matter, and ii) attributes of a respective change in magnitude of the detected optical energy 194 causing calibration of one or more optical sensors and/or optical monitoring stage 191 via measurement of a physically collected and measured sample.

In step 850, in response to detecting a subsequent change in the magnitude of the detected optical energy at one or more optical sensors is similar to a previous change in magnitude, the analyzer 140 retrieves the calibration information to calibrate the optical sensor and/or optical monitoring stage 191 based on previous calibration information in lieu of collecting the particulate in the fluid sample 110 to calibrate the optical sensor and/or optical monitoring stage 191.

Figure 9:
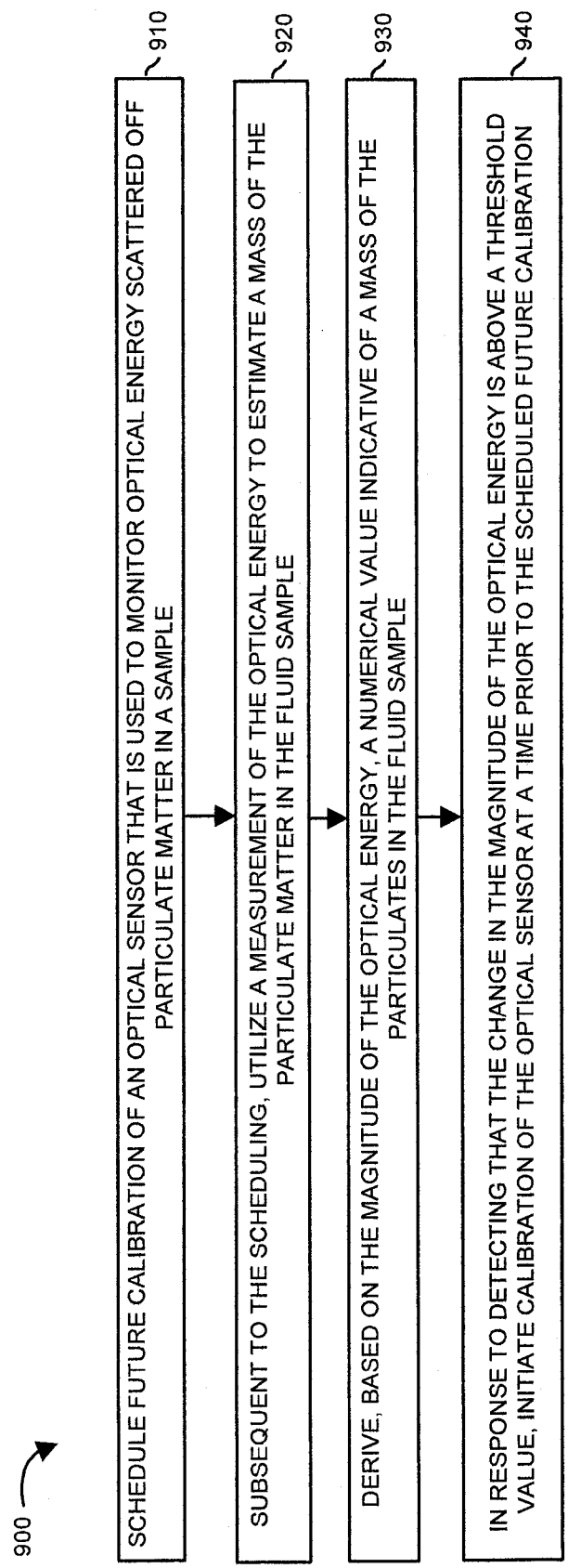

FIG. 9 is a flowchart 900 illustrating a method according to embodiments herein.

In step 910, analyzer 140 schedules future calibration of an optical sensor (in the optical monitoring stage 191) that is used to monitor optical energy 194. The optical energy 194 represents a portion of optical beam 192 scattering off of particulate matter in fluid sample 110.

In step 920, subsequent to the scheduling, analyzer 100 utilizes the measurement of detected optical energy 194 at one or more sensors 180 to estimate or calculate a mass of the particulate matter in the fluid sample.

In step 930, the analyzer 140 derives, based on the magnitude of the detected optical energy 194, a numerical value indicative of a mass of the particulates in the fluid sample 110. System 100 repeats this process to monitor the particulate matter over time.

In step 940, in response to detecting that the change in the magnitude of the detected optical energy 194 is above a threshold value, the analyzer 140 initiates calibration of the optical sensor at a time prior to the scheduled future calibration.

Figure 10:
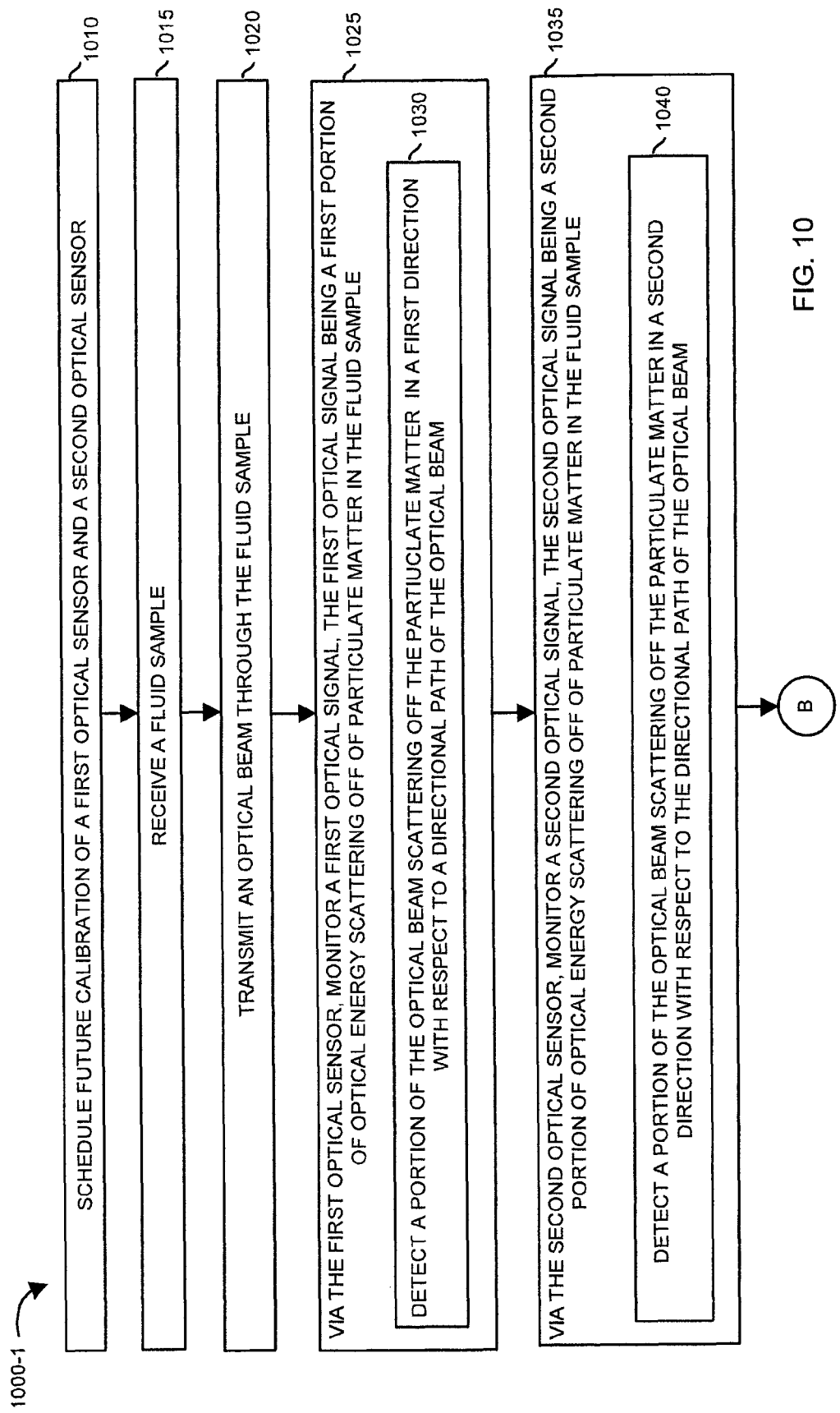
Figure 11:
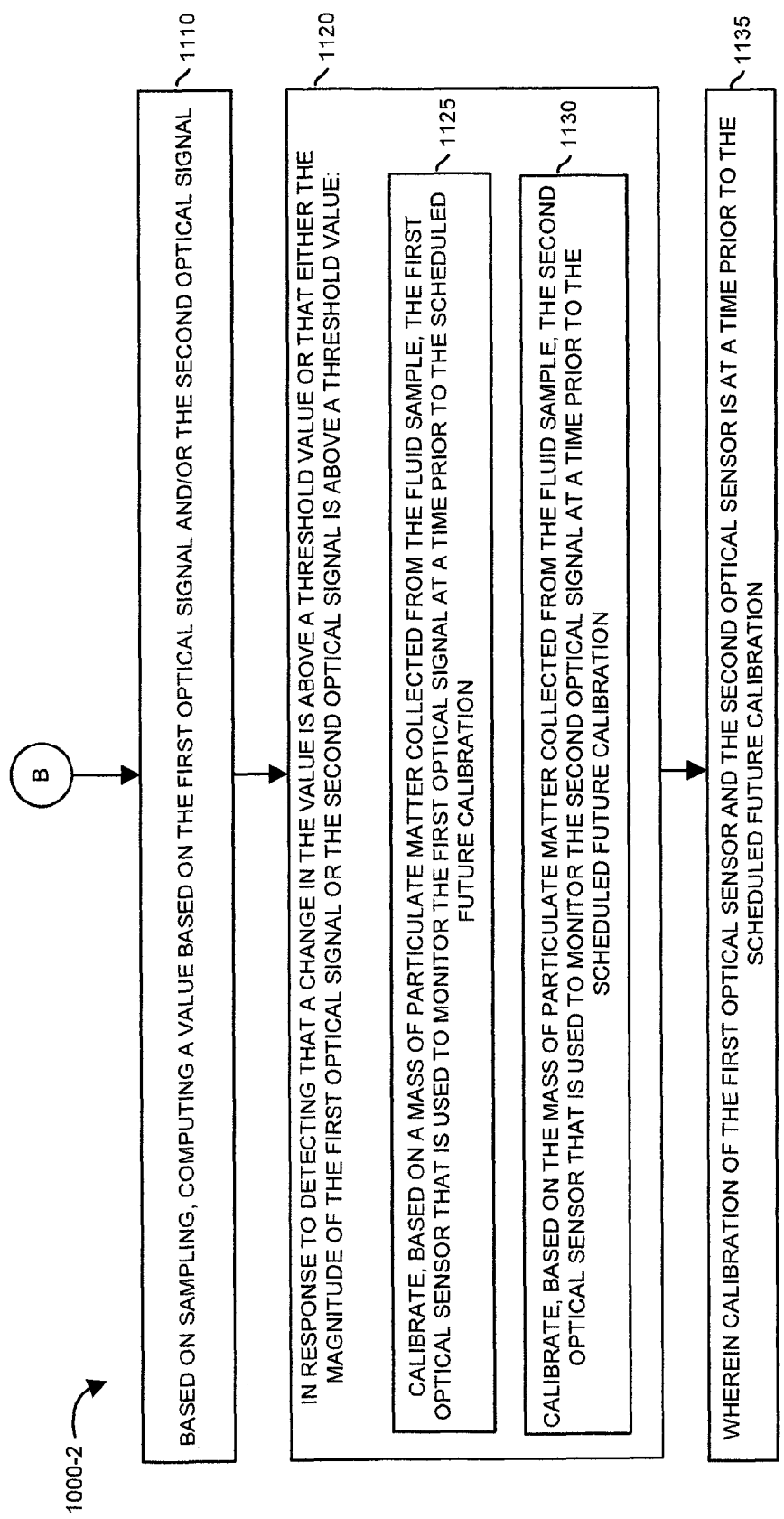

FIGS. 10 and 11 combine to form a flowchart 1000 (e.g., flowchart 1000-1 and flowchart 1000-2) of a method according to embodiments herein.

In step 1010, the analyzer 140 schedules future calibration of a first optical sensor and a second optical sensor used to measure optical energy 194 scattering off particulate matter.

In step 1015, the analyzer 140 receives a fluid sample 110.

In step 1020, the analyzer 140 transmits an optical beam 192 through the fluid sample 110.

In step 1025, via the first optical sensor 180-1, the analyzer 140 monitors a first optical scattering signal, the first optical scattering signal being a first portion of optical energy scattering off of particulate matter in the fluid sample 110.

In step 1030, the analyzer 140 detects scattering of a portion of the optical beam 192 in a first direction with respect to a directional path of the optical beam 192.

In step 1035, via the second optical sensor 180-2, the analyzer 140 monitors a second optical scattering signal, the second optical scattering signal being a second portion of optical energy scattering off of particulate matter in the fluid sample 110.

In step 1040, the analyzer 140 detects scattering of a portion of the optical beam 192 in a second direction with respect to the directional path of the optical beam 192.

In step 1110, based on sampling of the first optical scattering signal and the second optical scattering signal over time, the analyzer 140 tracks a value derived from the first optical scattering signal to the second optical scattering signal.

In step 1120, in response to detecting that a change in the value is beyond a threshold value (e.g., above a threshold value, below a threshold value, etc.) or that either the magnitude of the first optical scattering signal or the second optical scattering signal is above a threshold value: in step 1125, the analyzer 140 calibrates, based on a mass of particulate matter collected from the fluid sample 110, the first optical sensor 180-1 that is used to monitor the first optical scattering signal at a time prior to a scheduled future (e.g., next) calibration for the sensor. In step 1130, the analyzer 140 calibrates, based on the mass of particulate matter collected from the fluid sample 110, the second optical sensor that is used to monitor the second optical scattering signal at a time prior to the scheduled future calibration.

In step 1135, the analyzer 140 initiates calibration of the first optical sensor 180-1 and/or the second optical sensor 180-2 at a time prior to the scheduled future calibration for the sensor.

Figure 12:
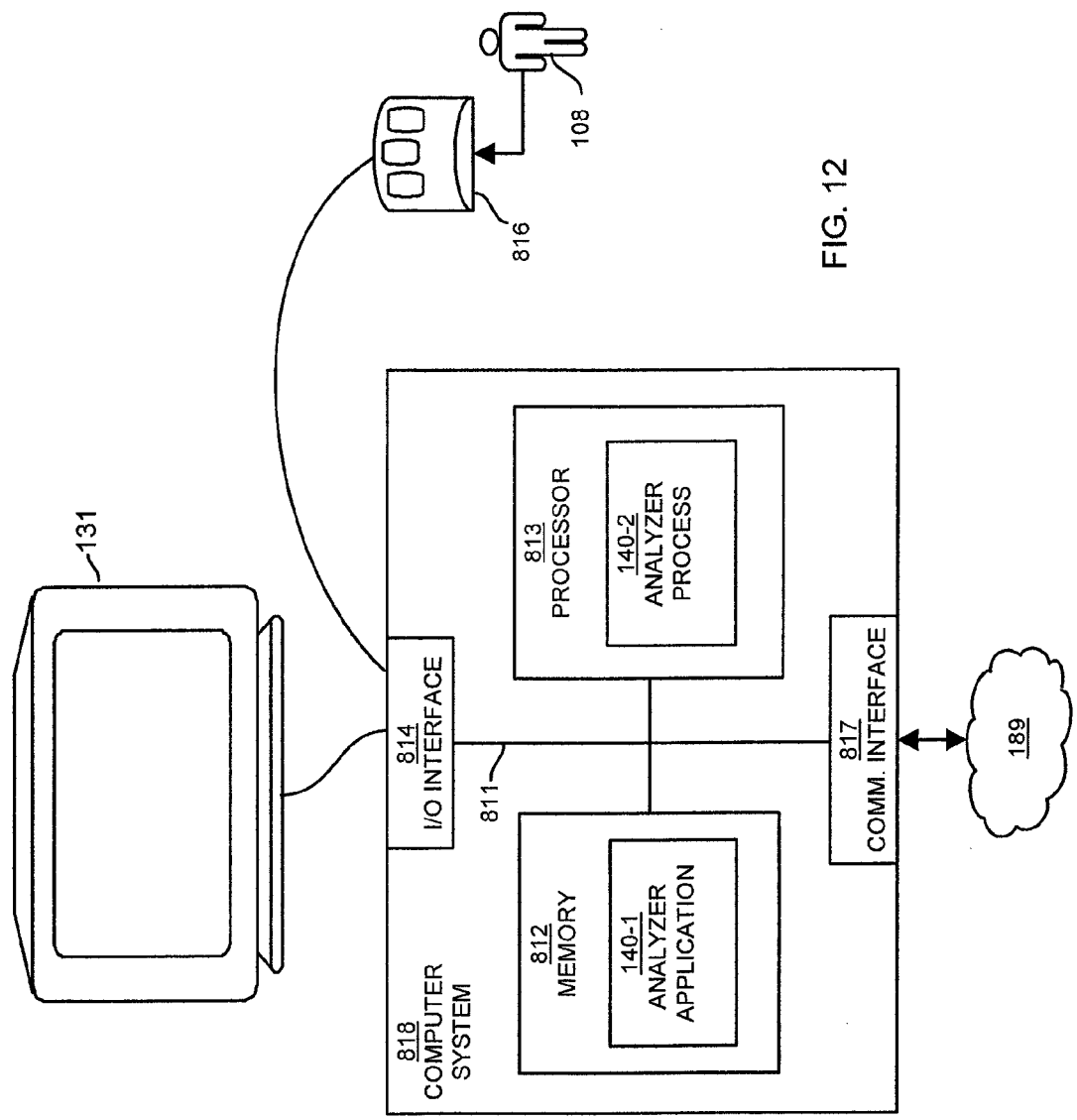
FIG. 12 is an example diagram illustrating a computer for executing software instructions to carry out operations according to embodiments herein.

FIG. 12 is a block diagram of an example architecture of a respective computer system 818 such as one or more computers, processes, etc., for implementing analyzer 140 and/or control of other aspects of system 100 according to embodiments herein. In other words, the analyzer 140 can include hardware and/or software that controls modules such as the temperature controller 160, dilution module 150, exhaust 199, etc., to facilitate calibration and subsequent generation of concentration values as described herein.

Computer system 818 can include one or more computerized devices such as personal computers, workstations, portable computing devices, consoles, network terminals, networks, processing devices, etc.

Note that the following discussion provides a basic example embodiment indicating how to carry out all or portions of the functionality associated with the analyzer 140 as discussed above and below. However, it should be noted again that the actual configuration for carrying out the analyzer 140 can vary depending on a respective application. For example, as previously discussed, computer system 818 can include one or multiple computers that carry out the processing as described herein.

As shown, computer system 818 of the present example includes an interconnect 811 coupling memory system 812, a processor 813, I/O interface 814, and a communications interface 817.

I/O interface 814 provides connectivity to peripheral devices such as repository and/or other devices 816 (if such devices are present) such as a keyboard, mouse (e.g., selection tool to move a cursor), display screen 131, etc.

Communications interface 817 enables the analyzer application 140-1 of computer system 818 to communicate over network 189 and, if necessary, retrieve data, update information, etc., from different sources.

As shown, memory system 812 can be encoded with instructions associated with analyzer application 140-1. The instructions support functionality as discussed above and as discussed further below. The analyzer application 140-1 (and/ or other resources as described herein) can be embodied as software code such as data and/or logic instructions on non-transitory computer readable storage medium such as a tangible and/or intangible computer readable medium, media, etc. such as memory or on another computer readable medium that supports processing functionality according to different embodiments described herein.

During operation of one embodiment, processor 813 accesses memory system 812 via the use of interconnect 811 in order to launch, run, execute, interpret or otherwise perform the logic instructions of the analyzer application 140-1. Execution of the analyzer application 140-1 produces processing functionality in analyzer process 140-2. In other words, the analyzer process 140-2 represents one or more portions of the analyzer 140 performing within or upon the processor 813 in the computer system 810.

It should be noted that, in addition to the analyzer process 140-2 that carries out method operations as discussed herein, other embodiments herein include the analyzer application 140-1 itself such as the un-executed or non-performing logic instructions and/or data, etc. As previously discussed, the analyzer application 140-1 may be stored on a non-transitory computer storage readable medium such as a floppy disk, hard disk, memory, optical medium, firmware, read only memory (ROM), etc.

Further Example Embodiments

Optical light scattering such as optical energy 194 as discussed herein can be elastic light scattering, that is, the scattering of light whose frequency is the same as the frequency of the incident light source whose output is always assumed to be constant. This method of measuring elastically scattered light (e.g., a combination of reflection, refraction and diffraction) is primarily a measurement of Mie scattering whereby the size of the particles being measured are approximately within the range of 0.05 to 100 micrometers and within a mass concentration range from 0.001 to 1000 milligrams of particulate mass per cubic meter of fluid sample. Within this range of particle sizes is the Mie scattering region, where the particle size and wavelength of light are approximately within the same order of magnitude.

By way of a non-limiting example, typical wavelengths used for measuring the Mie scattering of particulate matter can range from 400 to 1000 nanometers. However, note that any suitable wavelength can be used to generate optical beam 192 and measure scattered optical energy.

In general, a particle will scatter light with the greatest efficiency when the particle diameter of the particulate matter is equal to that of the incident light source wavelength.

As previously discussed, the intensity of scattered light or optical energy can be measured at a selected angle relative to the origin of the incident light source. Scattered light measured in the forward scattering region can range between 0 and 90 degrees and scattered light measured in the backward scattering region can range between 90 to 180 degrees.

Figure 13:
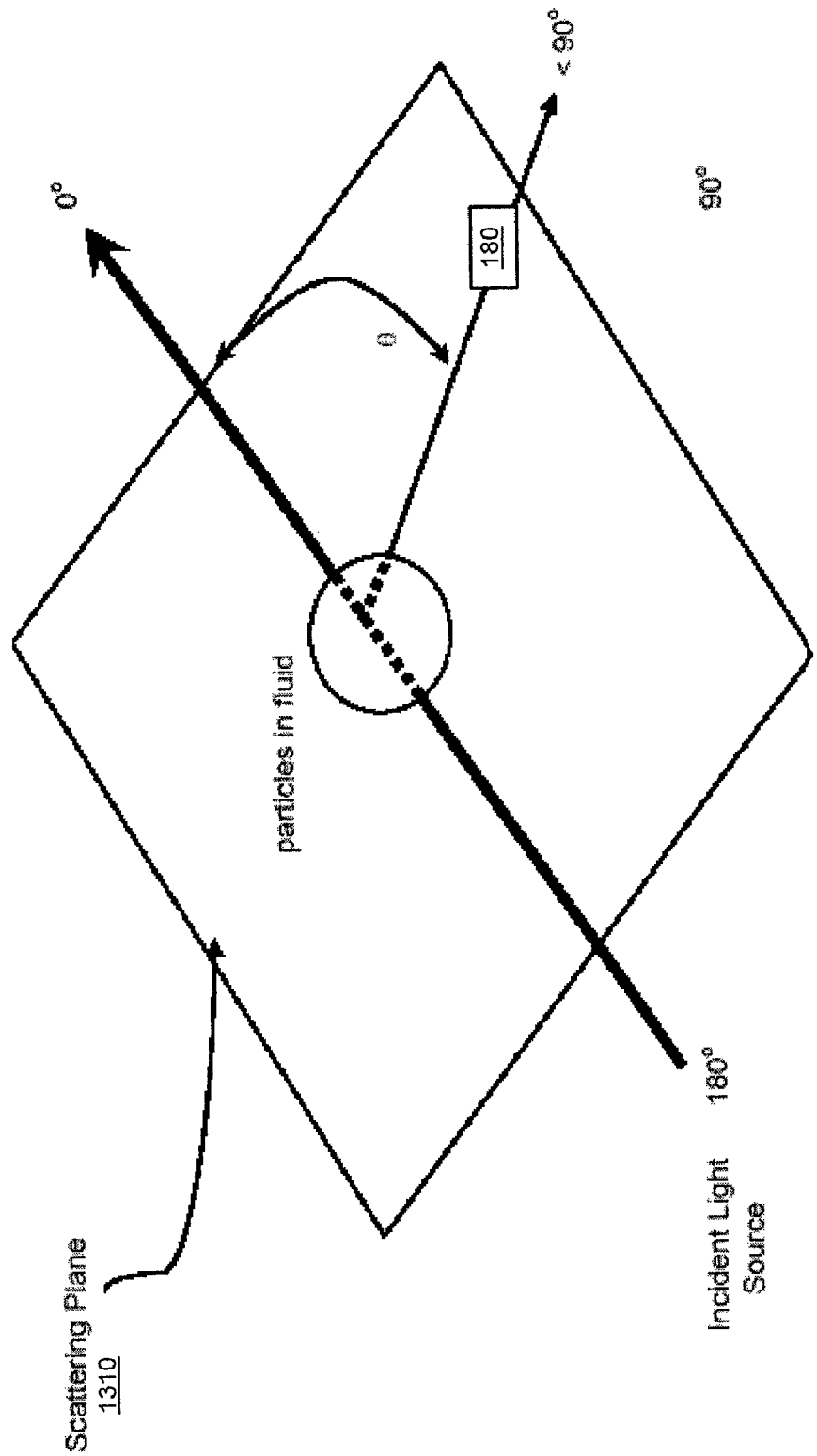
FIG. 13 is an example configuration of an optical system and scattering plane according to embodiments herein.

The plane formed by the incident light source (e.g., optical source 190) and the direction of the observation (scattered beam) is labeled as the scattering plane 1310 as shown in FIG. 13.

By way of a non-limiting example, a measurement of scattered light ($I_{FSavg}$) from a volume of particles within a fluid at a single forward scattering angle can be made over a period of time. As previously discussed, the particulate matter in the fluid can be collected and the particulate mass concentration ($PM_{avg}$) can be measured by a particulate mass collection stage 197 over the identical time averaging period that scattered light is measured. $PM_{avg}$ represents an actual physical mass measurement of collected particulate matter. $I_{FSavg}$ represents a measurement of scattered light during collection of the particulate matter.

The ratio of these measurements can then be used as a calibration factor to adjust the forward angle light scattering response to create a surrogate measurement of particulate mass concentration (PM*) during periods when the particulate matter collection stage is not being used. The equation below demonstrates this method of generating the surrogate measurement of particulate matter:

$$PM^* = I_{FS} * \left(\frac{PM_{avg}}{I_{FSavg}}\right)$$

Any change in the overall particle size distribution of the particles within the fluid can alter the amount of light scattering intensity measured. Furthermore, if characteristics of particles within the fluid happen to change, such as the particle refractive index, the light scattering intensity will also change. Therefore, a fluid sample carrying particles that are within a Mie scattering range can scatter light with a constant intensity only if all particle characteristics within the fluid remain constant. This is an unlikely condition. However, due to this unlikely condition, it can be understood that when a particulate mass measurement stage is not being utilized as a constant qualifier regarding the accuracy of the surrogate particulate mass measurement, it may be desirable to observe the intensity of light scattering from an additional point of reference or sensor in an effort to identify an indicator of changing particle characteristics within the fluid sample. In other words, embodiments herein can include monitoring the intensity of scattered optical energy at multiple sensors to more accurately or easily detect when there is a change associated with particulate matter in the fluid sample.

Figure 14:
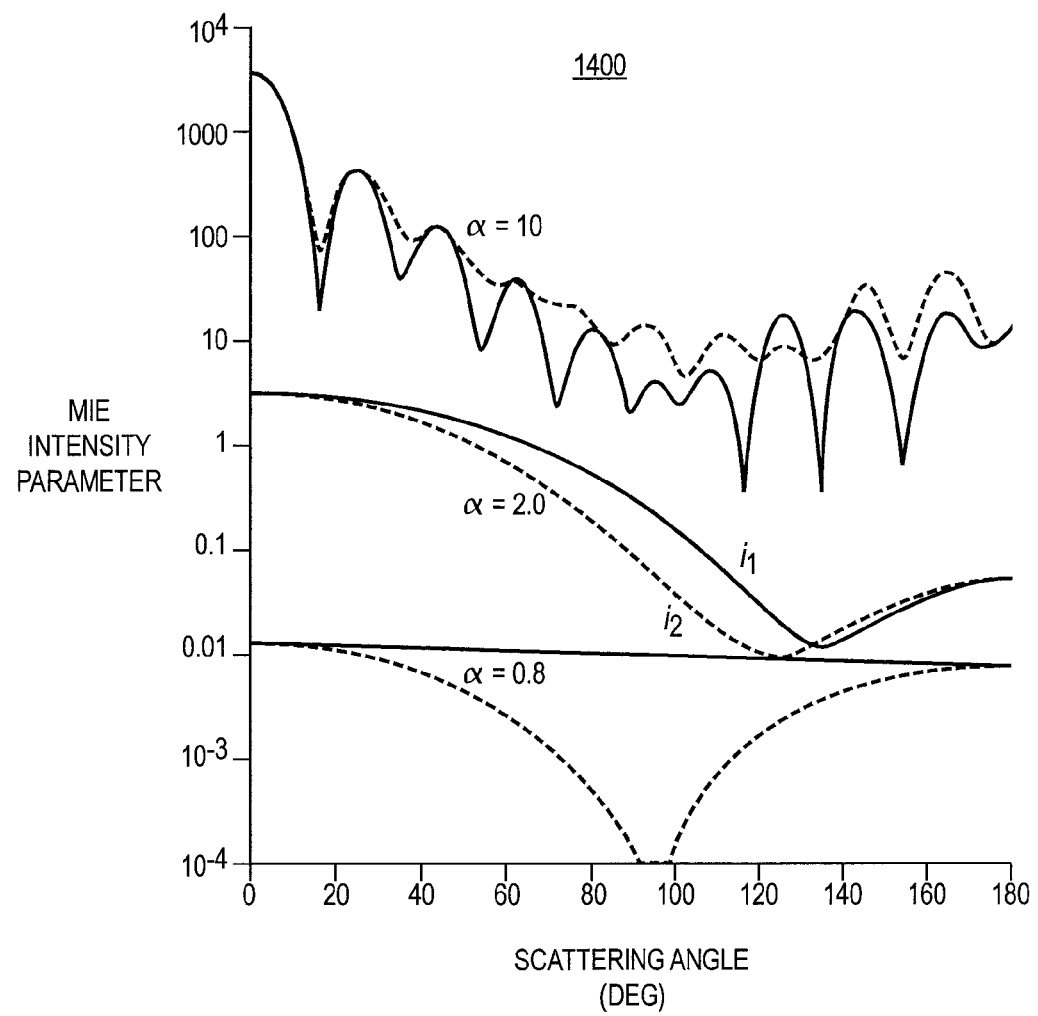
FIG. 14 is an example theoretical graph illustrating an intensity of Mie scattering for different particle size over a range of scattering angles according to embodiments herein.

As shown in FIG. 14, the Mie scattering intensity parameters (for i1 and i2) are plotted for three particle size parameters (0.8, 2, and 10) as a function of the observational scattering angle relative to an incident light source.

As shown via the graph in FIG. 14, the complexity of scattering intensity changes relative to particle size. The overall scattering magnitude changes with the scattering angle. As illustrated by the graph 1400, a first scattering angle can be selected that would provide a relatively stable measurement of light scattering (e.g., 25 degrees) and a second angle (e.g., 125-135 degrees) that could potentially offer a greater dependence upon particle characteristics.

When implementing an embodiment that measures optical energy at a single scattering angle, the method of measuring particulate matter may be limited by the frequency by which the particulate matter concentration surrogate calibration is repeated.

When implementing an embodiment that measures optical energy at two or more scattering angles, a ratio of the scattering intensities can be observed in real-time as an indicator of changing particle characteristics, such as a change in particle size of oxidized mercury in the fluid sample.

Figure 15:
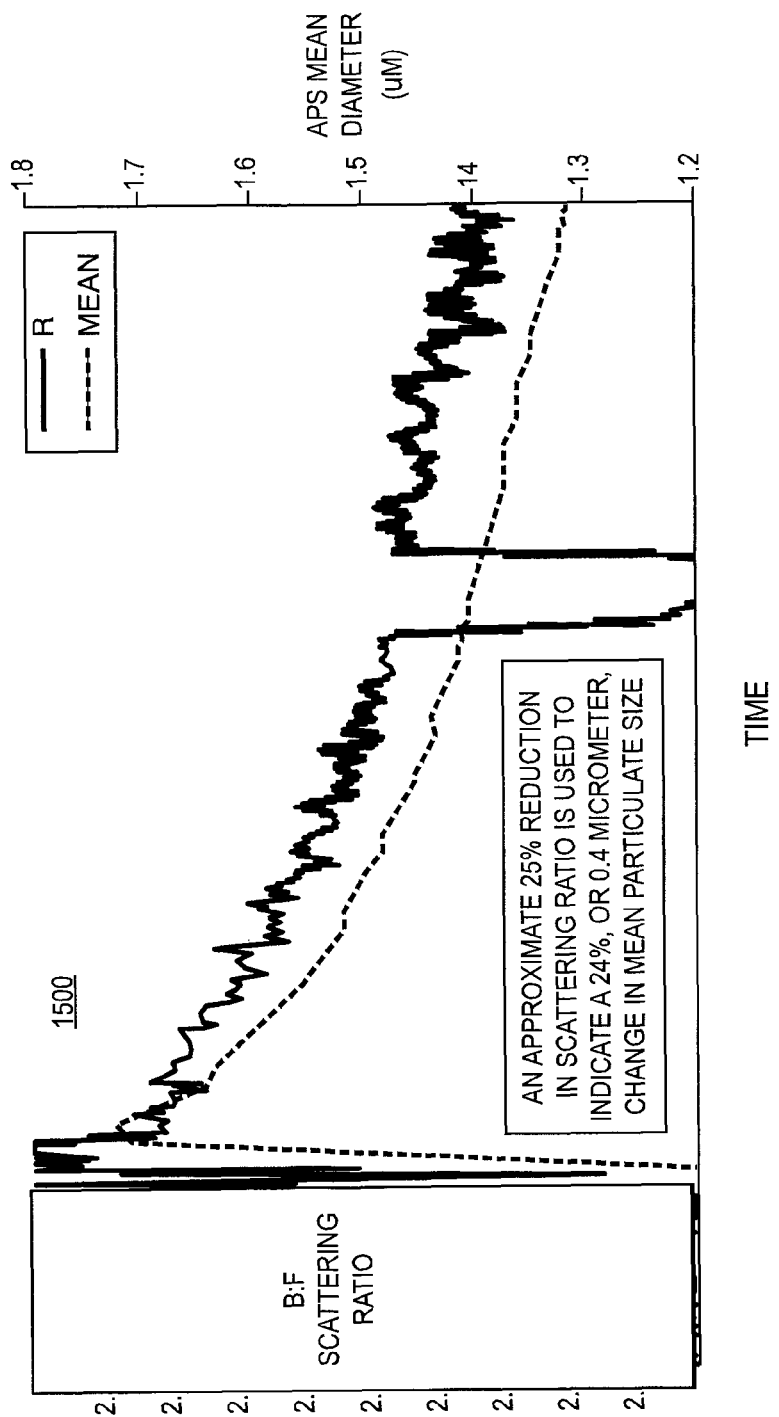
FIG. 15 is an example graph derived from experimental data illustrating how the a monitored value such as a ratio changes based on particle size according to embodiments herein.

In FIG. 15, and in accordance with the discussion above, data can be collected from sensors 180 to measure the scattering intensity of particulate matter such as a dry powder present in the fluid sample at two scattering angles; the first being a forward scattering angle and the second being a backward scattering angle with respect to the optical signal generated by optical source 190.

As shown, graph 1500 plots the ratio of scattering intensities along with a calculation of mean particle size for the particulate matter present in the fluid sample. This data in graph 1500 illustrates how measuring of and calculations based on an intensity of the scattered optical energy can be used to detect a change in particulate characteristics of particulate matter in the fluid sample 110.

In the example given above, it may be convenient to measure the particle diameter of the particulate within a fluid sample using sensitive laboratory methods.

Characteristics of monitored particulate matter that can change over time include parameters such as particle size, particle size distribution, refractive index, particle number concentration, etc. However, it may not be a simple matter of methodology to measure these particulate characteristics with laboratory equipment in an industrial setting. Embodiments herein include a method of measuring an indicator of particulate characteristic changes (i.e., an asymmetric factor) through use of multiple scattering angles. If the ratio of light scattering, or a secondary function thereof, change beyond a threshold value, an automatic particulate mass calibration can be initiated using a particulate mass sensing stage as discussed herein.

Figure 16:
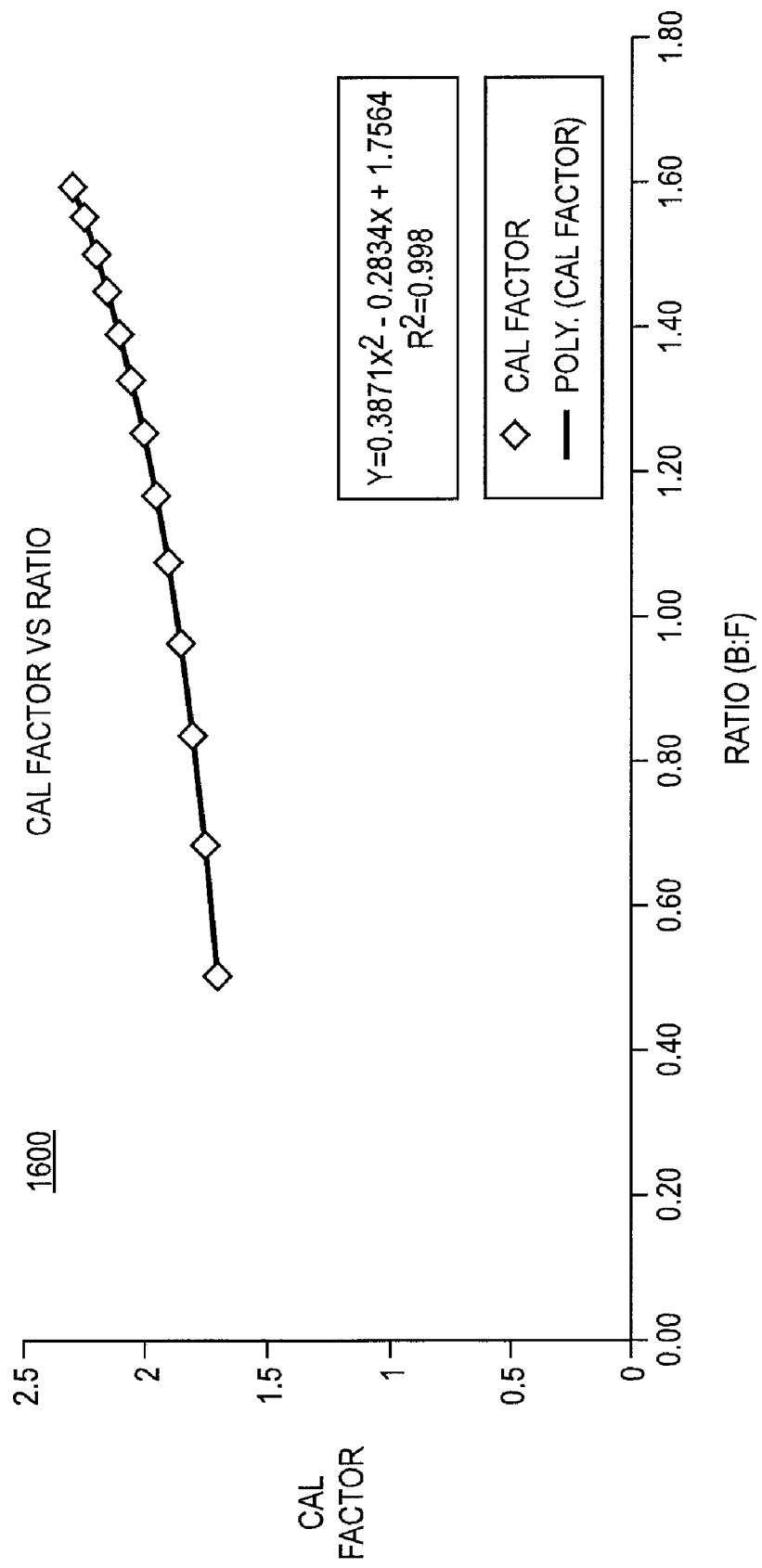
FIG. 16 is an example theoretical graph illustrating a magnitude of a calibration factor versus a magnitude ratio of backward to forward scattered optical energy according to embodiments herein.

FIG. 16 is an example diagram of graph 1600 illustrating a technique of utilizing forward and backward scattering intensities (as in Table 1 below) along with the surrogate calibration factor used to multiply the forward scattering response to gain a surrogate particulate matter concentration according to embodiments herein.

TABLE 1

| Forward | Backward | Ratio | Mean Diameter | Cal Factor | PM* |
|---|---|---|---|---|---|
| 1 | 0.5 | 0.50 | 1.20 | 1.7 | 1.7 |
| 1.1 | 0.75 | 0.68 | 1.34 | 1.75 | 1.925 |
| 1.2 | 1 | 0.83 | 1.47 | 1.8 | 2.16 |
| 1.3 | 1.25 | 0.96 | 1.61 | 1.85 | 2.405 |
| 1.4 | 1.5 | 1.07 | 1.74 | 1.9 | 2.66 |
| 1.5 | 1.75 | 1.17 | 1.88 | 1.95 | 2.925 |
| 1.6 | 2 | 1.25 | 2.01 | 2 | 3.2 |
| 1.7 | 2.25 | 1.32 | 2.15 | 2.05 | 3.485 |
| 1.8 | 2.5 | 1.39 | 2.28 | 2.1 | 3.78 |
| 1.9 | 2.75 | 1.45 | 2.42 | 2.15 | 4.085 |
| 2 | 3 | 1.50 | 2.55 | 2.2 | 4.4 |
| 2.1 | 3.25 | 1.55 | 2.69 | 2.25 | 4.725 |
| 2.2 | 3.5 | 1.59 | 2.83 | 2.3 | 5.06 |

Should the above table of data, that can be stored within the analyzer as a library of data, demonstrate a correlation of significant confidence, a calibration factor can then be derived from the ratio of scattering measurements, thereby extending the time interval between particulate mass concentration calibrations between the average forward scattering intensity and the particulate mass sensing stage as discussed above.

Note that the $2^{nd}$ order polynomial relationship in the graph 1600 is a non-limiting example of theoretical relationships that may be employed according to embodiments herein.

In accordance with further embodiments, system 100 can be configured to employ the use of multiple wavelengths as described in U.S. Pat. No. 6,055,052, the entire teachings of which are incorporated herein by this reference. In such an embodiment, the ratio of scattered optical energy may originate from a single light scattering observation angle. In further embodiments, the incident light source 190 can be configured to modulate between wavelengths within the Mie scattering range.

Another embodiment or variation of system 100 would be to measure at two or move wavelengths the scattering response at two or more observation angles in an effort to further enhance the resolution to which this system 100 can measure a change in particulate characteristics. In either condition, the above ratio method could also be employed.

Figure 17:
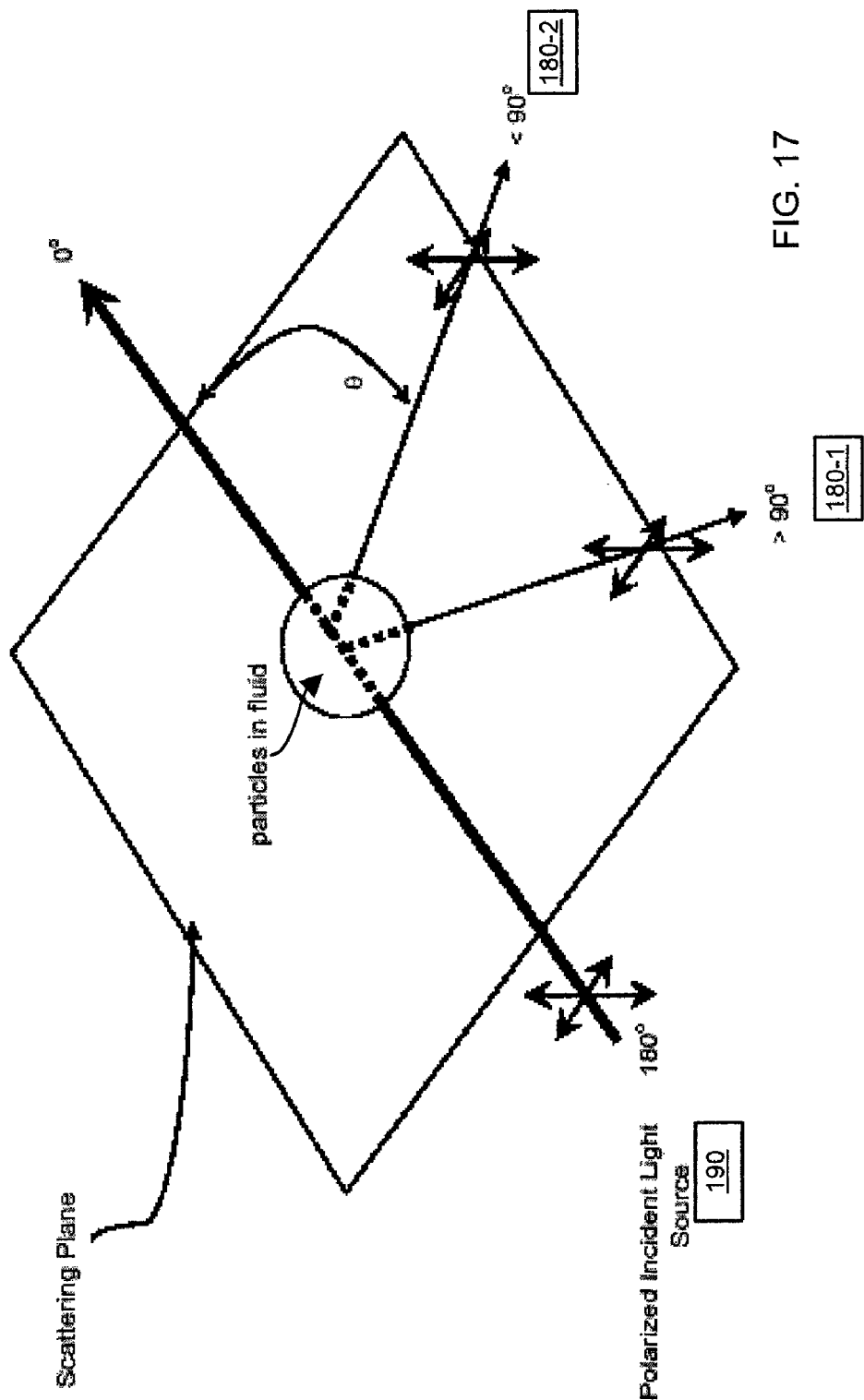
FIGS. 17 and 18 are example diagrams illustrating configurations of an optical system and a scattering plane according to embodiments herein.
Figure 18:
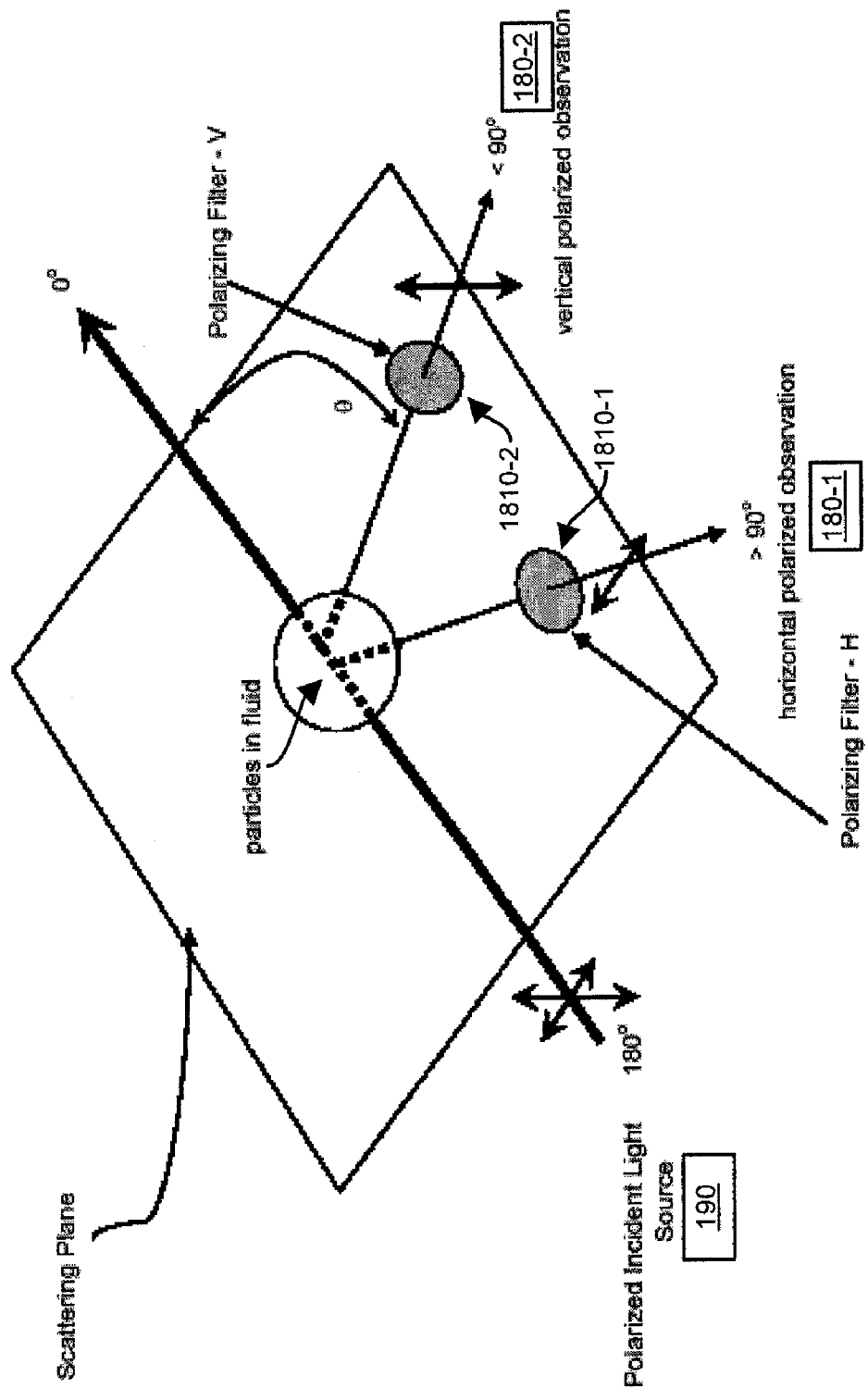

FIGS. 17 and 18 illustrate a technique of employing polarized light in accordance with embodiments herein. In such an embodiment, asymmetric measurements can be employed based on use of Mie scattering measurement with a polarized incident light source. By way of a non-limiting example, the optical source 190 can emit polarized light such as that emitted from a monochromatic laser diode.

In one embodiment, the scattering measurements that can be made using polarized light are similar to those described above and may include a single or multiple observation angles. However, the significant difference in this method is the portion of the polarized light scattered by the particulate matter in the fluid sample 110 retains an integrity of the polarized light.

In one embodiment, the polarized light scattering off particulate matter in the fluid sample 110 can be filtered such that the orthogonal components of polarized light (e.g., vertical and horizontal) can be measured independently at one or more observation angles. For example, polarized light on a first axis can be measured at a forward scattering angle; polarized light on a second axis can be measured at a backward scattering angle relative to the optical beam 192.

In an example embodiment as in FIG. 18, polarizing filters can be placed in a path of the scattered light such that one polarizing filter 1810-1 blocks horizontally polarized scattered light and allows vertically polarized scattered light to strike the first sensor 180-1 and second polarizing filter 1810-2 blocks vertically polarized scattered light and allows horizontally polarized scattered light to strike a second sensor 180-2.

In accordance with the embodiments as discussed above, the optical energy measured at the different scattering angles can be used to determine characteristics of particulate matter present in the fluid sample 110.

FIGS. 17 and 18 thus demonstrate a polarized light plane and a dual angle, dual observation scattering angle arrangement that independently measure the orthogonal components of scattered light according to embodiments herein. Using this arrangement and techniques such as the theory of surrogate particulate characteristic indicators through asymmetric measurement described herein, a similar approach can be utilized to provide an indicator that would initiate a calibration or maintenance event, or would draw from a table of accumulated analyzer data an extrapolated mass calibration factor for surrogate mass measurement.

Note again that techniques herein are well suited for detecting, measuring, monitoring, etc., particulate matter in an optical monitoring stage. However, it should be noted that embodiments herein are not limited to use in such applications and that the techniques discussed herein are suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. A method comprising:
receiving a fluid sample flowing through a conduit;

monitoring optical energy scattering off of particulate matter in the fluid sample, a magnitude of the optical energy varying depending on particulate matter present in the fluid sample;

detecting a change in the magnitude of the optical energy, the change in the magnitude indicative of a change in the particulate matter in the fluid sample; and in response to detecting the change in magnitude, initiating calibration of an optical sensor used to detect the optical energy.

2. The method as in claim 1, wherein initiating calibration of the optical sensor includes:

initiating physical collection of particulate matter present in the fluid sample;

calculating a mass of the particulate matter collected from the fluid sample; and calibrating the optical sensor based on the calculated mass of the particulate matter collected from the fluid sample.

3. The method as in claim 2, wherein initiating collection of the particulate matter present in the fluid sample occurs in response to detecting that the change in the magnitude of the optical energy is above a threshold value.

4. The method as in claim 3, wherein the change in the magnitude of the optical energy is indicative of a variation in a mass concentration of the particulates in the fluid sample.

5. The method as in claim 3, wherein the change in the magnitude of the optical energy is indicative of a variation in a composition of the particulates present in the fluid sample.

6. The method as in claim 3, wherein the change in the magnitude of the optical energy is indicative of a variation in a size of the particulates present in the fluid sample.

7. The method as in claim 2, wherein the change is a first change, the method further comprising:

in addition to calibrating the optical sensor, storing calibration information, the calibration information specifying: i) the calculated mass of the particulate matter, and ii) attributes of the first change in magnitude of the optical energy causing calibration of the optical sensor; and in response to detecting a subsequent change in the magnitude of the optical energy that is similar to the first change, retrieving the calibration information to calibrate the optical sensor in lieu of collecting the particulate in the fluid sample to calibrate the optical sensor.

8. The method as in claim 1 further comprising:

in response to detecting the change in magnitude of the optical energy, initiating collection of the particulate matter present in the fluid sample.

9. The method as in claim 1 further comprising:

transmitting an optical beam through the fluid sample as the fluid sample flows through the conduit; and wherein monitoring the optical energy includes detecting forward scattering of a portion of the optical beam, the forward scattering comprising scattering of the optical beam at an acute angle with respect to a path of the transmitted optical beam.

10. The method as in claim 1 further comprising:

transmitting an optical beam through the fluid sample as the fluid sample flows through the conduit; and wherein monitoring the optical energy includes detecting backward scattering of a portion of the optical beam, the backward scattering comprising scattered light of the optical beam at an obtuse angle with respect to a path of the transmitted optical beam.

11. The method as in claim 1 further comprising:

calculating, based on the magnitude of the optical energy, a numerical value indicative of a mass concentration of the particulate matter in the fluid sample; and in response to detecting the change in the magnitude, initiating execution of a diagnostic test routine to test hardware facilitating generation of the numerical value.

12. The method as in claim 1 further comprising:

receiving a gas sample from a flue;

diluting the gas sample with a dilution gas;

heating the diluted gas sample; and wherein the received fluid sample flowing through the conduit is the heated, diluted gas sample.

13. The method as in claim 1 further comprising:

monitoring the fluid sample as the fluid sample flows through the conduit, the conduit being vertically disposed.

14. The method as in claim 1 further comprising:

transmitting an optical beam through the fluid sample; and wherein monitoring the optical energy includes:

utilizing a first optical sensor device to detect light from the optical beam scattering off the particulate matter in the fluid sample; and utilizing a second optical sensor device to detect light from the optical beam scattering off the particulate matter in the fluid sample.

15. The method as in claim 1 further comprising:

transmitting an optical beam through the fluid sample; and wherein monitoring the optical energy includes:

detecting a scattering of a portion of the optical beam in a forward path with respect to a directional path of the optical beam; and detecting a scattering of a portion of the optical beam in a backward path with respect to a directional path of the optical beam.

16. The method as in claim 1 further comprising:

scheduling future calibration of an optical sensor that is used to monitor the optical energy;

subsequent to the scheduling, utilizing a measurement of the optical energy to estimate a mass of the particulate matter in the fluid sample;

deriving, based on the magnitude of the optical energy, a numerical value indicative of a mass of the particulates in the fluid sample; and in response to detecting that the change in the magnitude of the optical energy signal is above a threshold value, initiating calibration of the optical sensor at a time prior to the scheduled future calibration.

17. The method as in claim 1, wherein monitoring the optical energy includes:

monitoring the optical energy scattering off of the particulate matter at two or more wavelengths.

18. The method as in claim 1, wherein monitoring the optical energy includes:

monitoring the optical energy scattering off of the particulate matter at multiple scattering angles.

19. The method as in claim 1, wherein monitoring the optical energy includes:

monitoring components of polarized light scattering off of the particulate matter.

20. A method comprising:

receiving a fluid sample;

monitoring a first optical signal, the first optical signal being a first portion of optical energy scattering off of particulate matter in the fluid sample;

monitoring a second optical signal, the second optical signal being a second portion of optical energy scattering off of particulate matter in the fluid sample;

computing a value based on the first optical signal and the second optical signal; and in response to detecting a change with respect to the value:

calibrating, based on a mass of particulate matter physically collected from the fluid sample, a first optical sensor that is used to monitor the first optical signal; and calibrating, based on the mass of particulate matter physically collected from the fluid sample, a second optical sensor that is used to monitor the second optical signal.

21. The method as in claim 20 further comprising:

transmitting an optical beam through the fluid sample;

wherein monitoring the first optical signal includes detecting scattering of a portion of the optical beam in a first direction with respect to a directional path of the optical beam; and wherein monitoring the second optical signal includes detecting scattering of a portion of the optical beam in a second direction with respect to the directional path of the optical beam.

22. The method as in claim 20 further comprising:

scheduling future calibration of the first optical sensor and the second optical sensor; and in response to detecting that the change in the value is above a threshold value, initiating calibration of the first optical sensor and the second optical sensor at a time prior to the scheduled future calibration.

23. A system comprising:

a conduit through which to pass a fluid sample flow, the fluid sample flow including particulate matter;

at least one optical sensor to monitor optical energy scattering off of the particulate matter in the fluid sample flow, a magnitude of the optical energy varying depending on particulate matter present in the fluid sample flow;

an analyzer to detect a change in the optical energy, the change in the optical energy indicative of a change in the particulate matter in the fluid sample flow, the analyzer configured to initiate recalibration of the at least one optical sensor in response to the change in the optical energy.

24. The system as in claim 23, wherein the conduit is vertically disposed to facilitate a flow of the particulate matter through the conduit.

25. The system as in claim 23 further comprising:

a probe disposed in a flue to receive a gas sample including particulate matter;

a dilution stage to dilute the gas sample with a dilution gas;

a heater to heat the diluted gas sample;

a channel through which to convey the heated, diluted gas sample to the conduit; and wherein the fluid sample flow comprises the heated, diluted gas sample received from the channel.

26. The system as in claim 25, wherein the probe, dilution stage, and heater are disposed in the flue.

27. The system as in claim 23, wherein the at least one optical sensor includes a first optical sensor and a second optical sensor; and wherein the analyzer initiates recalibration of the first optical sensor and the second optical sensor in response to a condition in which a ratio of optical energy detected by the first optical sensor and a magnitude optical energy detected by the second optical sensor is greater than a threshold value.

28. The method as in claim 23, wherein the change in the optical energy is indicative of a variation in a mass concentration of the particulates in the fluid sample.

29. The method as in claim 23, wherein the change in the optical energy is indicative of a variation in a composition of the particulates in the fluid sample.

30. The method as in claim 23, wherein the change in the optical energy is indicative of a variation in a size of the particulates in the fluid sample.

* * * * *